United States Patent
Lachance et al.

(10) Patent No.: US 8,063,224 B2
(45) Date of Patent: Nov. 22, 2011

(54) AZACYCLOALKANE DERIVATIVES AS INHIBITORS OF STEAROYL-COENZYME A DELTA-9 DESATURASE

(75) Inventors: Nicolas Lachance, Pierrefonds (CA); Chun Sing Li, Dollard-des-Ormeaux (CA); Jean-Philippe Leclerc, Laval (CA); Yeeman K. Ramtohul, Pierrefonds (CA)

(73) Assignee: Merck Canada Inc., Quebec (CA)

( * ) Notice: Subject to any disclaimer, the term of this patent is extended or adjusted under 35 U.S.C. 154(b) by 1026 days.

(21) Appl. No.: 11/998,501

(22) Filed: Nov. 30, 2007

(65) Prior Publication Data

US 2008/0132542 A1 Jun. 5, 2008

Related U.S. Application Data

(60) Provisional application No. 60/872,216, filed on Dec. 1, 2006, provisional application No. 60/898,900, filed on Feb. 1, 2007.

(51) Int. Cl.
C07D 401/00 (2006.01)
A61K 31/445 (2006.01)
(52) U.S. Cl. ........................................ 546/207; 514/326
(58) Field of Classification Search .................. 546/207; 514/326
See application file for complete search history.

(56) References Cited

U.S. PATENT DOCUMENTS

| | | | | |
|---|---|---|---|---|
| 3,489,757 | A * | 1/1970 | Volker et al. | 544/369 |
| 2005/0119251 | A1 | 6/2005 | Fu et al. | |
| 2005/0234033 | A1 | 10/2005 | Anandan et al. | |
| 2008/0182838 | A1 | 7/2008 | Leblanc et al. | |
| 2009/0099200 | A1 * | 4/2009 | Li et al. | 514/254.02 |

FOREIGN PATENT DOCUMENTS

| | | |
|---|---|---|
| CA | 2 533 897 A1 | 2/2005 |
| CA | 2 580 787 A1 | 3/2006 |
| CA | 2 580 855 A1 | 3/2006 |
| WO | WO 97/26258 | 7/1997 |
| WO | WO 2006/034279 A1 | 3/2006 |
| WO | WO 2006/034312 A1 | 3/2006 |
| WO | WO 2006/034315 A2 | 3/2006 |
| WO | WO 2006/034315 A3 | 3/2006 |
| WO | WO 2006/034338 A1 | 3/2006 |
| WO | WO 2006/034341 A2 | 3/2006 |
| WO | WO 2006/034341 A3 | 3/2006 |
| WO | WO 2006/034440 A2 | 3/2006 |
| WO | WO 2006/034440 A3 | 3/2006 |
| WO | WO 2006/034441 A1 | 3/2006 |
| WO | WO 2006/086445 A2 | 8/2006 |
| WO | WO 2006/086445 A3 | 8/2006 |
| WO | WO 2006/086447 A2 | 8/2006 |
| WO | WO 2006/086447 A3 | 8/2006 |
| WO | WO 2006/101521 A2 | 9/2006 |
| WO | WO 2006/101521 A3 | 9/2006 |
| WO | WO 2006/125181 A2 | 11/2006 |
| WO | WO 2006/125181 A3 | 11/2006 |
| WO | WO 2006/130986 A1 | 12/2006 |
| WO | WO 2007/009236 A1 | 1/2007 |
| WO | WO 2007/038865 A1 | 4/2007 |
| WO | WO 2007/056846 A1 | 5/2007 |
| WO | WO 2007/071023 A1 | 6/2007 |
| WO | WO 2007/134457 A1 | 11/2007 |
| WO | WO 2007/143823 A1 | 12/2007 |
| WO | WO 2007/143824 A1 | 12/2007 |
| WO | WO 2008/017161 A1 | 2/2008 |
| WO | WO 2008/046226 A1 | 4/2008 |
| WO | WO 2008/089580 A1 | 7/2008 |

OTHER PUBLICATIONS

Zhao, H. et al., "Discovery of 1-(4-phenoxypiperidin-1-yl)-2-arylaminoethanone stearoyl-CoA desaturase 1 inhibitors" Bioorganic & Medicinal Chemistry Letters, vol. 17, pp. 3388-3391, 2007.

Liu, G. et al., "Discovery of Potent, Selective, Orally Bioavailable Stearoyl-CoA Desaturase 1 Inhibitors" J. Med. Chem., vol. 50, pp. 3086-3100, 2007.

* cited by examiner

*Primary Examiner* — Rita Desai
*Assistant Examiner* — John Mabry
(74) *Attorney, Agent, or Firm* — Kenrick L. Vidale; John C. Todaro

(57) ABSTRACT

Azacycloalkane derivatives of structural formula I are selective inhibitors of stearoyl-coenzyme A delta-9 desaturase (SCD1) relative to other known stearoyl-coenzyme A desaturases. The compounds of the present invention are useful for the prevention and treatment of conditions related to abnormal lipid synthesis and metabolism, including cardiovascular disease, such as atherosclerosis; obesity; diabetes; neurological disease; metabolic syndrome; insulin resistance; and liver steatosis.

(I)

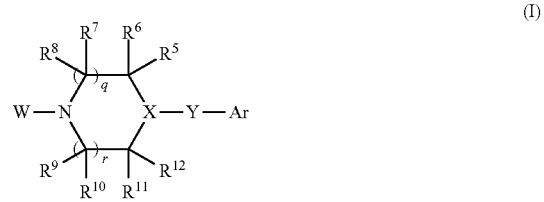

13 Claims, No Drawings

AZACYCLOALKANE DERIVATIVES AS INHIBITORS OF STEAROYL-COENZYME A DELTA-9 DESATURASE

CROSS-REFERENCE TO RELATED APPLICATIONS

The present invention is related to U.S. provisional application Ser. Nos. 60/872,216, filed Dec. 1, 2006, and 60/898,900, filed Feb. 1, 2007; the contents of each of which are hereby incorporated by reference.

FIELD OF THE INVENTION

The present invention relates to azacycloalkane derivatives which are inhibitors of stearoyl-coenzyme A delta-9 desaturase (SCD) and the use of such compounds to control, prevent and/or treat conditions or diseases mediated by SCD activity. The compounds of the present invention are useful for the control, prevention and treatment of conditions and diseases related to abnormal lipid synthesis and metabolism, including cardiovascular disease, such as atherosclerosis; obesity; diabetes; neurological disease; metabolic syndrome; insulin resistance; cancer; and hepatic steatosis.

BACKGROUND OF THE INVENTION

At least three classes of fatty acyl-coenzyme A (CoA) desaturases (delta-5, delta-6 and delta-9 desaturases) are responsible for the formation of double bonds in mono- and polyunsaturated fatty acyl-CoAs derived from either dietary sources or de novo synthesis in mammals. The delta-9 specific stearoyl-CoA desaturases (SCDs) catalyze the rate-limiting formation of the cis-double bond at the C9-C10 position in monounsaturated fatty acyl-CoAs. The preferred substrates are stearoyl-CoA and palmitoyl-CoA, with the resulting oleoyl and palmitoleoyl-CoA as the main components in the biosynthesis of phospholipids, triglycerides, cholesterol esters and wax esters (Dobrzyn and Natami, *Obesity Reviews*, 6: 169-174 (2005)).

The rat liver microsomal SCD protein was first isolated and characterized in 1974 (Strittmatter et al., *PNAS*, 71: 4565-4569 (1974)). A number of mammalian SCD genes have since been cloned and studied from various species. For example, two genes have been identified from rat (SCD1 and SCD2, Thiede et al., *J. Biol. Chem.*, 261, 13230-13235 (1986)), Mihara, K., *J. Biochem. (Tokyo)*, 108: 1022-1029 (1990)); four genes from mouse (SCD1, SCD2, SCD3 and SCD4) (Miyazaki et al., *J. Biol. Chem.*, 278: 33904-33911 (2003)); and two genes from human (SCD1 and ACOD4 (SCD2)), (Zhang, et al., *Biochem. J.*, 340: 255-264 (1991); Beiraghi, et al., *Gene*, 309: 11-21 (2003); Zhang et al., *Biochem. J.*, 388: 135-142 (2005)). The involvement of SCDs in fatty acid metabolism has been known in rats and mice since the 1970's (Oshino, N., *Arch. Biochem. Biophys.*, 149: 378-387 (1972)). This has been further supported by the biological studies of a) Asebia mice that carry the natural mutation in the SCD1 gene (Zheng et al., *Nature Genetics*, 23: 268-270 (1999)), b) SCD1-null mice from targeted gene deletion (Ntambi, et al., *PNAS*, 99: 11482-11486 (2002), and c) the suppression of SCD1 expression during leptin-induced weight loss (Cohen et al., *Science*, 297: 240-243 (2002)). The potential benefits of pharmacological inhibition of SCD activity has been demonstrated with anti-sense oligonucleotide inhibitors (ASO) in mice (Jiang, et al., *J. Clin. Invest.*, 115: 1030-1038 (2005)). ASO inhibition of SCD activity reduced fatty acid synthesis and increased fatty acid oxidation in primary mouse hepatocytes. Treatment of mice with SCD-ASOs resulted in the prevention of diet-induced obesity, reduced body adiposity, hepatomegaly, steatosis, postprandial plasma insulin and glucose levels, reduced de novo fatty acid synthesis, decreased the expression of lipogenic genes, and increased the expression of genes promoting energy expenditure in liver and adipose tissues. Thus, SCD inhibition represents a novel therapeutic strategy in the treatment of obesity and related metabolic disorders.

There is compelling evidence to support that elevated SCD activity in humans is directly implicated in several common disease processes. For example, there is an elevated hepatic lipogenesis to triglyceride secretion in non-alcoholic fatty liver disease patients (Diraison, et al., *Diabetes Metabolism*, 29: 478-485 (2003)); Donnelly, et al., *J. Clin. Invest.*, 115: 1343-1351 (2005)). The postprandial de novo lipogenesis is significantly elevated in obese subjects (Marques-Lopes, et al., *American Journal of Clinical Nutrition*, 73: 252-261 (2001)). There is a significant correlation between a high SCD activity and an increased cardiovascular risk profile including elevated plasma triglycerides, a high body mass index and reduced plasma HDL (Attie, et al., *J. Lipid Res.*, 43: 1899-1907 (2002)). SCD activity plays a key role in controlling the proliferation and survival of human transformed cells (Scaglia and Igal, *J. Biol. Chem.*, (2005)).

Other than the above mentioned anti-sense oligonucleotides, inhibitors of SCD activity include non-selective thia-fatty acid substrate analogs [B. Behrouzian and P. H. Buist, *Prostaglandins, Leukotrienes, and Essential Fatty Acids*, 68: 107-112 (2003)], cyclopropenoid fatty acids (Raju and Reiser, *J. Biol. Chem.*, 242: 379-384 (1967)), certain conjugated long-chain fatty acid isomers (Park, et al., *Biochim. Biophys. Acta*, 1486: 285-292 (2000)), a series of pyridazine derivatives disclosed in published international patent application publications WO 2005/011653, WO 2005/011654, WO 2005/011656, WO 2005/011656, and WO 2005/011657, all assigned to Xenon Pharmaceuticals, Inc., and a series of heterocyclic derivatives disclosed international patent application publications WO 2006/014168, WO 2006/034279, WO 2006/034312, WO 2006/034315, WO 2006/034338, WO 2006/034341, WO 2006/034440, WO 2006/034441, and WO 2006/034446, all assigned to Xenon Pharmaceuticals, Inc.

The present invention is concerned with novel azacycloalkane derivatives as inhibitors of stearoyl-CoA delta-9 desaturase which are useful in the treatment and/or prevention of various conditions and diseases mediated by SCD activity including those related, but not limited, to elevated lipid levels, as exemplified in non-alcoholic fatty liver disease, cardiovascular disease, obesity, diabetes, metabolic syndrome, and insulin resistance.

The role of stearoyl-coenzyme A desaturase in lipid metabolism has been described by M. Miyazaki and J. M. Ntambi, *Prostaglandins, Leukotrienes, and Essential Fatty Acids*, 68: 113-121 (2003). The therapeutic potential of the pharmacological manipulation of SCD activity has been described by A. Dobryzn and J. M. Ntambi, in "Stearoyl-CoA desaturase as a new drug target for obesity treatment," *Obesity Reviews*, 6: 169-174 (2005).

SUMMARY OF THE INVENTION

The present invention relates to azacycloalkane derivatives of structural formula I:

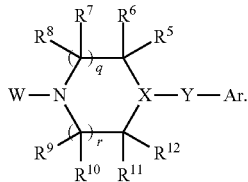

(I)

These azacycloalkane derivatives are effective as inhibitors of SCD. They are therefore useful for the treatment, control or prevention of disorders responsive to the inhibition of SCD, such as diabetes, insulin resistance, lipid disorders, obesity, atherosclerosis, and metabolic syndrome.

The present invention also relates to pharmaceutical compositions comprising the compounds of the present invention and a pharmaceutically acceptable carrier.

The present invention also relates to methods for the treatment, control, or prevention of disorders, diseases, or conditions responsive to inhibition of SCD in a subject in need thereof by administering the compounds and pharmaceutical compositions of the present invention.

The present invention also relates to methods for the treatment, control, or prevention of Type 2 diabetes, insulin resistance, obesity, lipid disorders, atherosclerosis, and metabolic syndrome by administering the compounds and pharmaceutical compositions of the present invention.

The present invention also relates to methods for the treatment, control, or prevention of obesity by administering the compounds of the present invention in combination with a therapeutically effective amount of another agent known to be useful to treat the condition.

The present invention also relates to methods for the treatment, control, or prevention of Type 2 diabetes by administering the compounds of the present invention in combination with a therapeutically effective amount of another agent known to be useful to treat the condition.

The present invention also relates to methods for the treatment, control, or prevention of atherosclerosis by administering the compounds of the present invention in combination with a therapeutically effective amount of another agent known to be useful to treat the condition.

The present invention also relates to methods for the treatment, control, or prevention of lipid disorders by administering the compounds of the present invention in combination with a therapeutically effective amount of another agent known to be useful to treat the condition.

The present invention also relates to methods for treating metabolic syndrome by administering the compounds of the present invention in combination with a therapeutically effective amount of another agent known to be useful to treat the condition.

DETAILED DESCRIPTION OF THE INVENTION

The present invention is concerned with azacycloalkane derivatives useful as inhibitors of SCD. Compounds of the present invention are described by structural formula I:

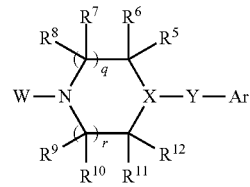

(I)

or a pharmaceutically acceptable salt thereof; wherein
q is 0 or 1;
r is 0 or 1;
Z is O, S, or $NR^4$;
X—Y is N—C(O), N—$CR^aR^b$, $CR^{14}$—O, $CR^{14}$—$S(O)_{0-2}$, or $CR^{13}$—$CR^aR^b$;
$R^a$ and $R^b$ are each independently hydrogen or $C_{1-3}$ alkyl, wherein alkyl is optionally substituted with one to three substituents independently selected from fluorine and hydroxy;
W is heteroaryl selected from the group consisting of:

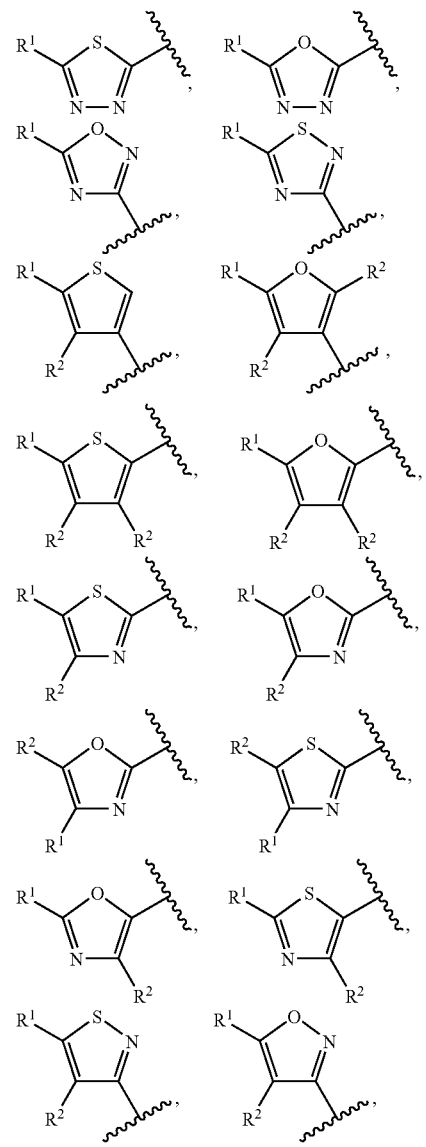

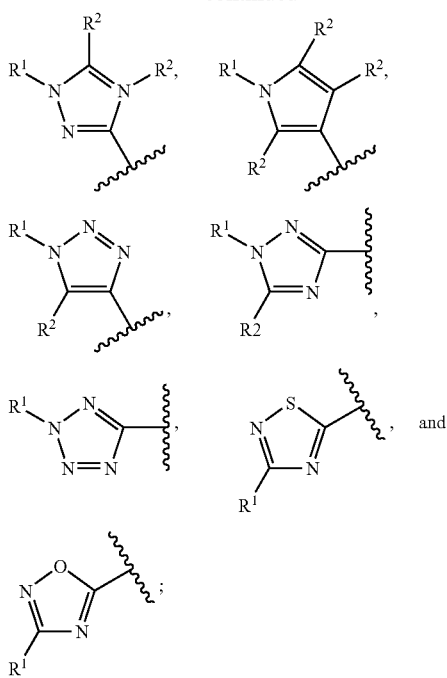

$R^1$ is heteroaryl selected from the group consisting of:

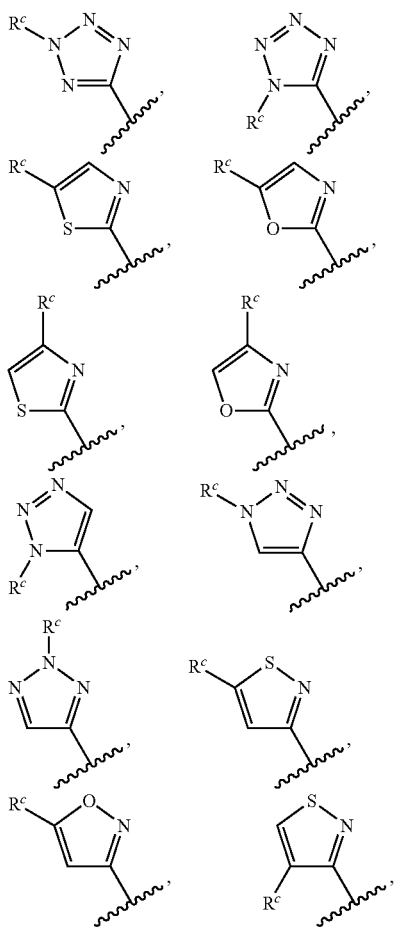

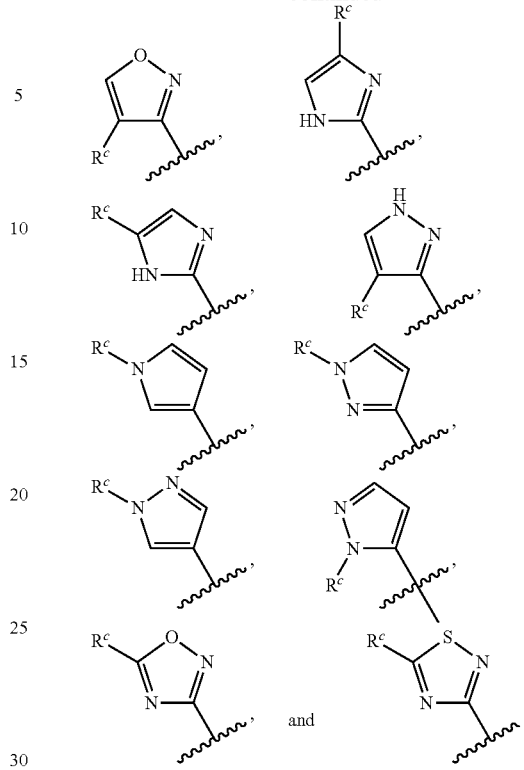

wherein $R^c$ is $-(CH_2)_m CO_2 H$, $-(CH_2)_m CO_2 C_{1-3}$ alkyl, $-(CH_2)_m-Z-(CH_2)_p CO_2 H$, or $-(CH_2)_m-Z-(CH_2)_p CO_2 C_{1-3}$ alkyl; wherein any methylene ($CH_2$) carbon atom in $(CH_2)_m$ or $(CH_2)_p$ is optionally substituted with one hydroxy, one amino, or one to two fluorines; and wherein said $R^1$ heteroaryl ring is optionally substituted with one substituent independently selected from the group consisting of cyano, halogen, $C_{1-4}$ alkyl, $C_{1-4}$ alkoxy, $C_{1-4}$ alkylthio, $C_{1-4}$ alkylsulfonyl, and trifluoromethyl;

each $R^2$ is independently selected from the group consisting of:
hydrogen,
halogen,
hydroxy,
cyano,
amino,
nitro,
$C_{1-4}$ alkyl, optionally substituted with one to five fluorines,
$C_{1-4}$ alkoxy, optionally substituted with one to five fluorines,
$C_{1-4}$ alkylthio, optionally substituted with one to five fluorines,
$C_{1-4}$ alkylsulfonyl,
carboxy,
$C_{1-4}$ alkyloxycarbonyl, and
$C_{1-4}$ alkylcarbonyl;

Ar is phenyl, naphthyl, or heteroaryl optionally substituted with one to five $R^3$ substituents; each $R^3$ is independently selected from the group consisting of:
$C_{1-6}$ alkyl,
$C_{2-6}$ alkenyl,
$(CH_2)_n$-phenyl,
$(CH_2)_n$-naphthyl,
$(CH_2)_n$-heteroaryl,
$(CH_2)_n$-heterocyclyl, (CH$_2$)$_n$C$_{3-7}$ cycloalkyl,
halogen,
nitro,
(CH$_2$)$_n$OR$^4$,
(CH$_2$)$_n$N(R$^4$)$_2$,
(CH$_2$)$_n$C≡N,
(CH$_2$)$_n$CO$_2$R$^4$,
(CH$_2$)$_n$NR$^4$SO$_2$R$^4$
(CH$_2$)$_n$SO$_2$N(R$^4$)$_2$,
(CH$_2$)$_n$S(O)$_{0-2}$R$^4$,
(CH$_2$)$_n$NR$^4$C(O)N(R$^4$)$_2$,
(CH$_2$)$_n$C(O)N(R$^4$)$_2$,
(CH$_2$)$_n$NR$^4$C(O)R$^4$,
(CH$_2$)$_n$NR$^4$CO$_2$R$^4$,
(CH$_2$)$_n$C(O)R$^4$,
O(CH$_2$)$_n$C(O)N(R$^4$)$_2$,
(CH$_2$)$_s$—Z—(CH$_2$)$_t$-phenyl,
(CH$_2$)$_s$—Z—(CH$_2$)$_t$-naphthyl,
(CH$_2$)$_s$—Z—(CH$_2$)$_t$-heteroaryl,
(CH$_2$)$_s$—Z—(CH$_2$)$_t$-heterocyclyl,
(CH$_2$)$_s$—Z—(CH$_2$)$_t$—C$_{3-7}$ cycloalkyl,
(CH$_2$)$_s$—Z—(CH$_2$)$_t$—OR$^4$,
(CH$_2$)$_s$—Z—(CH$_2$)$_t$—N(R$^4$)$_2$,
(CH$_2$)$_s$—Z—(CH$_2$)$_t$—NR$^4$SO$_2$R$^4$,
(CH$_2$)$_s$—Z—(CH$_2$)$_t$—C≡N,
(CH$_2$)$_s$—Z—(CH$_2$)$_t$—CO$_2$R$^4$,
(CH$_2$)$_s$—Z—(CH$_2$)$_t$—SO$_2$N(R$^4$)$_2$,
(CH$_2$)$_s$—Z—(CH$_2$)$_t$—S(O)$_{0-2}$R$^4$,
(CH$_2$)$_s$—Z—(CH$_2$)$_t$—NR$^4$C(O)N(R$^4$)$_2$,
(CH$_2$)$_s$—Z—(CH$_2$)$_t$—C(O)N(R$^4$)$_2$,
(CH$_2$)$_s$—Z—(CH$_2$)$_t$—NR$^4$C(O)R$^4$,
(CH$_2$)$_s$—Z—(CH$_2$)$_t$—NR$^4$CO$_2$R$^4$,
(CH$_2$)$_s$—Z—(CH$_2$)$_t$—C(O)R$^4$,
CF$_3$,
CH$_2$CF$_3$,
OCF$_3$, and
OCH$_2$CF$_3$;
in which phenyl, naphthyl, heteroaryl, cycloalkyl, and heterocyclyl are optionally substituted with one to three substituents independently selected from halogen, hydroxy, C$_{1-4}$ alkyl, trifluoromethyl, and C$_{1-4}$ alkoxy, optionally substituted with one to five fluorines; and wherein any methylene (CH$_2$) carbon atom in R$^3$ is optionally substituted with one to two groups independently selected from fluorine, hydroxy, and C$_{1-4}$ alkyl; or two substituents when on the same methylene (CH$_2$) group are taken together with the carbon atom to which they are attached to form a cyclopropyl group;
each R$^4$ is independently selected from the group consisting of
hydrogen,
C$_{1-6}$ alkyl,
(CH$_2$)$_n$-phenyl,
(CH$_2$)$_n$-heteroaryl,
(CH$_2$)$_n$-naphthyl, and
(CH$_2$)$_n$C$_{3-7}$ cycloalkyl;
wherein alkyl, phenyl, heteroaryl, and cycloalkyl are optionally substituted with one to three groups independently selected from halogen, C$_{1-4}$ alkyl, and C$_{1-4}$ alkoxy; or two R$^4$ groups together with the atom to which they are attached form a 4- to 8-membered mono- or bicyclic ring system optionally containing an additional heteroatom selected from O, S, NH, and NC$_{1-4}$ alkyl;
R$^5$, R$^6$, R$^7$, R$^8$, R$^9$, R$^{10}$, R$^{11}$, and R$^{12}$ are each independently hydrogen, fluorine, or C$_{1-3}$ alkyl, wherein alkyl is optionally substituted with one to three substituents independently selected from fluorine and hydroxy;
R$^{13}$ is hydrogen, C$_{1-3}$ alkyl, fluorine, or hydroxy;

each R$^{14}$ is hydrogen or C$_{1-3}$ alkyl;
each m is independently an integer from 0 to 4;
each p is independently an integer from 1 to 3;
each n is independently an integer from 0 to 2;
each s is independently an integer from 1 to 3; and
each t is independently an integer from 1 to 3.

In one embodiment of the compounds of the present invention, m is 1 or 2. In a class of this embodiment, m is 1.

In a second embodiment of the compounds of the present invention, q and r are both 1, affording a 6-membered piperidine ring.

In a third embodiment of the compounds of the present invention, q is 1 and r is 0, affording a 5-membered pyrrolidine ring.

In a fourth embodiment of the compounds of the present invention, q and r are both 0, affording a 4-membered azetidine ring.

In a fifth embodiment of the compounds of the present invention, X—Y is N—C(O). In a class of this embodiment, Ar is phenyl substituted with one to three R$^3$ substituents as defined above.

In a sixth embodiment of the compounds of the present invention, X—Y is CH—O. In a class of this embodiment, Ar is phenyl substituted with one to three R$^3$ substituents as defined above.

In a seventh embodiment of the compounds of the present invention, X—Y is CH—S(O)$_p$. In a class of this embodiment, Ar is phenyl substituted with one to three R$^3$ substituents as defined above.

In an eighth embodiment of the compounds of the present invention, X—Y is N—CR$^a$R$^b$. In a class of this embodiment, Ar is phenyl substituted with one to three R$^3$ substituents as defined above. In yet another class of this embodiment, R$^a$ and R$^b$ are hydrogen and Ar is phenyl substituted with one to three R$^3$ substituents.

In a ninth embodiment of the compounds of the present invention, X—Y is CR$^{13}$—CR$^a$R$^b$. In a class of this embodiment, Ar is phenyl substituted with one to three R$^3$ substituents as defined above. In yet another class of this embodiment, R$^a$, R$^b$, and R$^{13}$ are hydrogen and Ar is phenyl substituted with one to three R$^3$ substituents.

In a further embodiment of the compounds of the present invention, R$^5$, R$^6$, R$^7$, R$^8$, R$^9$, R$^{10}$, R$^{11}$, and R$^{12}$ are each hydrogen.

In yet a further embodiment, W is heteroaryl selected from the group consisting of:

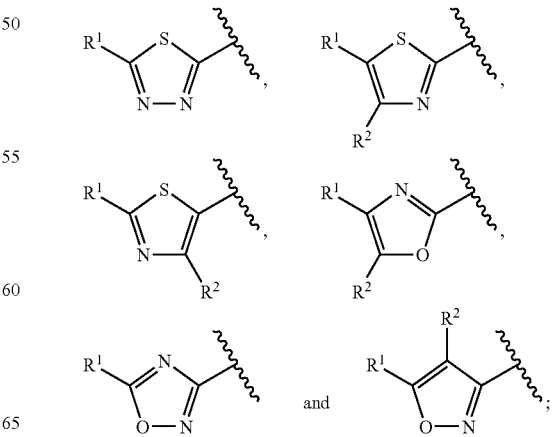

wherein $R^1$ and $R^2$ are as defined above. In a class of this embodiment, $R^2$ is hydrogen.

In another class of this embodiment, W is

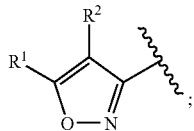

wherein $R^1$ and $R^2$ are as defined above.

In a yet a further embodiment, $R^1$ is heteroaryl selected from the group consisting of

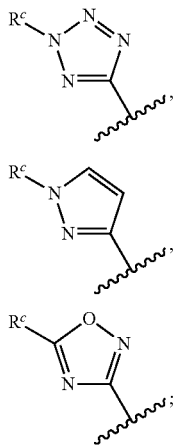
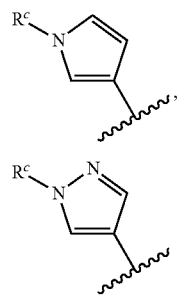

wherein $R^c$ is —$CH_2CO_2H$ or —$CH_2CO_2C_{1-3}$ alkyl. In a class of this embodiment, $R^1$ is

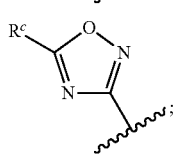

In yet a further embodiment of the compounds of the present invention, q and r are both 1; X—Y is CH—O; W is heteroaryl selected from the group consisting of:

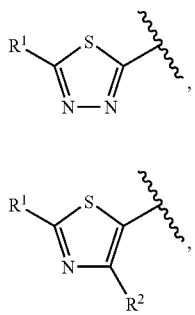
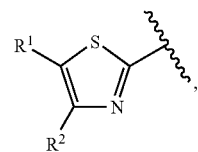
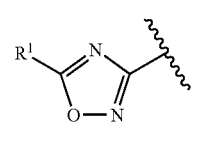

and $R^1$ is heteroaryl selected from the group consisting of:

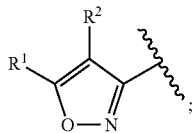
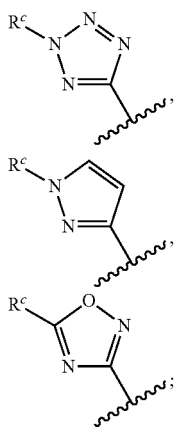
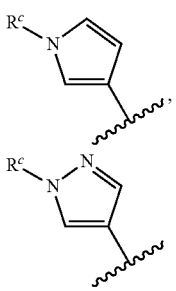
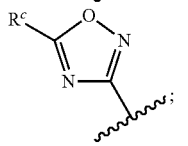

wherein $R^c$ is —$CH_2CO_2H$ or —$CH_2CO_2C_{1-3}$ alkyl.

In a class of this embodiment, $R^2$, $R^5$, $R^6$, $R^7$, $R^8$, $R^9$, $R^{10}$, $R^{11}$, and $R^{12}$ are each hydrogen.

In another class of this embodiment, W is

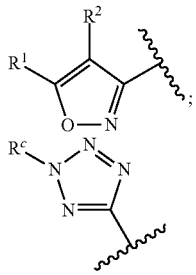

wherein $R^c$ is —$CH_2CO_2H$ or —$CH_2CO_2C_{1-3}$ alkyl.

In a subclass of this class, $R^2$, $R^5$, $R^6$, $R^7$, $R^8$, $R^9$, $R^{10}$, $R^{11}$, and $R^{12}$ are each hydrogen.

Illustrative, but nonlimiting examples, of compounds of the present invention that are useful as inhibitors of SCD are the following:

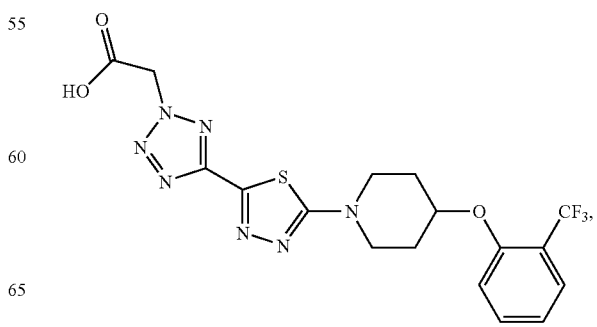

-continued

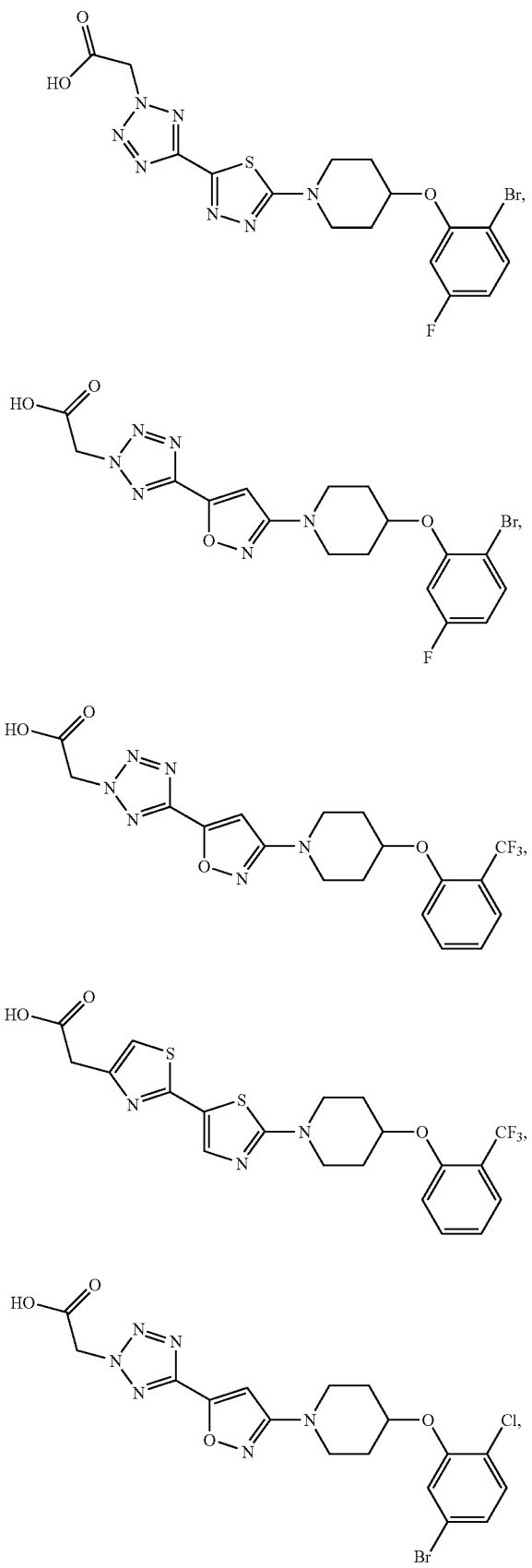

-continued

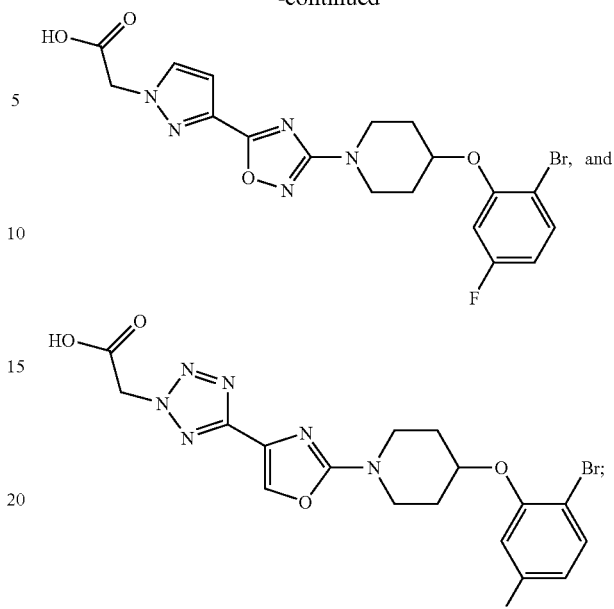

and pharmaceutically acceptable salts thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkenyl" shall mean straight or branched-chain alkenes having the specified number of carbon atoms. Examples of alkenyl include vinyl, 1-propenyl, 1-butenyl, 2-butenyl, and the like.

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkylsulfinyl" refers to straight or branched chain alkylsulfoxides of the number of carbon atoms specified (e.g., $C_{1-6}$ alkylsulfinyl), or any number within this range [i.e., methylsulfinyl (MeSO—), ethylsulfinyl, isopropylsulfinyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, 2-oxopiperidin-1-yl, 2-oxopyrrolidin-1-yl, and 2-oxoazetidin-1-yl, and the like.

"Heteroaryl" means an aromatic or partially aromatic heterocycle that contains at least one ring heteroatom selected from O, S and N. Heteroaryls thus includes heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl (in particular, 1,3,4-oxadiazol-2-yl and 1,2,4-oxadiazol-3-yl), thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

Compounds of structural formula I may contain one or more asymmetric centers and can thus occur as racemates and racemic mixtures, single enantiomers, diastereomeric mixtures and individual diastereomers. The present invention is meant to comprehend all such isomeric forms of the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetyl, pivaloyl, benzoyl, and aminoacyl, can be employed. Included are those esters and acyl groups known in the art for modifying the solubility or hydrolysis characteristics for use as sustained-release or prodrug formulations.

Solvates, in particular hydrates, of the compounds of structural formula I are included in the present invention as well.

The subject compounds are useful in a method of inhibiting the stearoyl-coenzyme A delta-9 desaturase enzyme (SCD) in a patient such as a mammal in need of such inhibition comprising the administration of an effective amount of the compound. The compounds of the present invention are therefore useful to control, prevent, and/or treat conditions and diseases mediated by high or abnormal SCD enzyme activity.

Thus, one aspect of the present invention concerns a method of treating hyperglycemia, diabetes or insulin resistance in a mammalian patient in need of such treatment, which comprises administering to said patient an effective amount of a compound in accordance with structural formula I or a pharmaceutically salt or solvate thereof.

A second aspect of the present invention concerns a method of treating non-insulin dependent diabetes mellitus (Type 2 diabetes) in a mammalian patient in need of such treatment comprising administering to the patient an antidiabetic effective amount of a compound in accordance with structural formula I.

A third aspect of the present invention concerns a method of treating obesity in a mammalian patient in need of such treatment comprising administering to said patient a compound in accordance with structural formula I in an amount that is effective to treat obesity.

A fourth aspect of the invention concerns a method of treating metabolic syndrome and its sequelae in a mammalian patient in need of such treatment comprising administering to said patient a compound in accordance with structural formula I in an amount that is effective to treat metabolic syndrome and its sequelae. The sequelae of the metabolic syndrome include hypertension, elevated blood glucose levels, high triglycerides, and low levels of HDL cholesterol.

A fifth aspect of the invention concerns a method of treating a lipid disorder selected from the group consisting of dyslipidemia, hyperlipidemia, hypertriglyceridemia, hypercholesterolemia, low HDL and high LDL in a mammalian patient in need of such treatment comprising administering to said patient a compound in accordance with structural formula I in an amount that is effective to treat said lipid disorder.

A sixth aspect of the invention concerns a method of treating atherosclerosis in a mammalian patient in need of such treatment comprising administering to said patient a compound in accordance with structural formula I in an amount effective to treat atherosclerosis.

A seventh aspect of the invention concerns a method of treating cancer in a mammalian patient in need of such treatment comprising administering to said patient a compound in accordance with structural formula I in an amount effective to treat cancer.

A further aspect of the invention concerns a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) fatty liver disease, (21) polycystic ovary syndrome, (22) sleep-disordered breathing, (23) metabolic syndrome, and (24) other conditions and disorders where insulin resistance is a component, in a mammalian patient in need of such treatment comprising administering to the patient a compound in accordance with structural formula I in an amount that is effective to treat said condition.

Yet a further aspect of the invention concerns a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) fatty liver disease, (21) polycystic ovary syndrome, (22) sleep-disordered breathing, (23) metabolic syndrome, and (24) other conditions and disorders where insulin resistance is a component, and other conditions and disorders where insulin resistance is a component, in a mammalian patient in need of such treatment comprising administering to the patient a compound in accordance with structural formula I in an amount that is effective to delay the onset of said condition.

Yet a further aspect of the invention concerns a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) fatty liver disease, (21) polycystic ovary syndrome, (22) sleep-disordered breathing, (23) metabolic syndrome, and (24) other conditions and disorders where insulin resistance is a component, in a mammalian patient in need of such treatment comprising administering to the patient a compound in accordance with structural formula I in an amount that is effective to reduce the risk of developing said condition.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent, such as a mouse, species can be treated. However, the method can also be practiced in other species, such as avian species (e.g., chickens).

The present invention is further directed to a method for the manufacture of a medicament for inhibiting stearoyl-coenzyme A delta-9 desaturase enzyme activity in humans and animals comprising combining a compound of the present invention with a pharmaceutically acceptable carrier or diluent. More particularly, the present invention is directed to the use of a compound of structural formula I in the manufacture of a medicament for use in treating a condition selected from the group consisting of hyperglycemia, Type 2 diabetes, insulin resistance, obesity, and a lipid disorder in a mammal, wherein the lipid disorder is selected from the group consisting of dyslipidemia, hyperlipidemia, hypertriglyceridemia, hypercholesterolemia, low HDL, and high LDL.

The subject treated in the present methods is generally a mammal, preferably a human being, male or female, in whom inhibition of stearoyl-coenzyme A delta-9 desaturase enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of stearoyl-coenzyme A delta-9 desaturase (SCD) enzyme activity may be demonstrated by the following microsomal and whole-cell based assays:

I. SCD-Induced Rat Liver Microsome Assay:

The activity of compounds of formula I against the SCD enzyme is determined by following the conversion of radiolabeled-stearoyl-CoA to oleoyl-CoA using SCD1-induced rat liver microsome and a previously published procedure with some modifications (Joshi, et al., *J. Lipid Res.,* 18: 32-36 (1977)). After feeding wistar rats with a high carbohydrate/fat-free rodent diet (LabDiet #5803, Purina) for 3 days, the SCD-induced livers were homogenized (1:10 w/v) in 250 mM sucrose, 1 mM EDTA, 5 mM DTT and 50 mM Tris-HCl (pH 7.5). After a 20 min centrifugation (18,000×g/4° C.) to remove tissue and cell debris, the microsome was prepared by a 100,000×g centrifugation (60 min) with the resulting pellet suspended in 100 mM sodium phosphate, 20% glycerol and 2 mM DTT. Test compound in 2 µL DMSO was incubated for 15 min at room temperature with 180 µL of the microsome (typically at about 100 µg/mL, in Tris-HCl buffer (100 mM, pH 7.5), ATP (5 mM), Coenzyme A (0.1 mM), Triton X-100 (0.5 mM) and NADH (2 mM)). The reaction was initiated by the addition of 20 µL of [$^3$H]-Stearoyl-CoA (final concentration at 2 µM with the radioactivity concentration at 1 µCi/mL), and terminated by the addition of 150 µL of 1N sodium hydroxide. After 60 min at room temperature to hydrolyze the oleoyl-CoA and stearoyl-CoA, the solution was acidified by the addition of 150 µL of 15% phosphoric acid (v/v) in ethanol supplemented with 0.5 mg/mL stearic acid and 0.5 mg/mL oleic acid. [$^3$H]-oleic acid and [$^3$H]-stearic acid were then quantified on a HPLC that is equipped with a C-18 reverse phase column and a Packard Flow Scintillation Analyzer. Alternatively, the reaction mixture (80 µL) was mixed with a calcium chloride/charcoal aqueous suspension (100 µL of 15% (w/v) charcoal plus 20 µL of 2 N $CaCl_2$). The resulting mixture was centrifuged to precipitate the radioactive fatty acid species into a stable pellet. Tritiated water from SCD-catalyzed desaturation of 9,10-[$^3$H]-stearoyl-CoA was quantified by counting 50 µL of the supernant on a scintillation counter.

II. Whole Cell-Based SCD (Delta-9), Delta-5 and Delta-6 Desaturase Assays:

Human HepG2 cells were grown on 24-well plates in MEM media (Gibco cat#11095-072) supplemented with 10% heat-inactivated fetal bovine serum at 37° C. under 5% $CO_2$ in a humidified incubator. Test compound dissolved in the media was incubated with the subconfluent cells for 15 min at 37° C. [1-$^{14}$C]-stearic acid was added to each well to a final concentration of 0.05 µCi/mL to detect SCD-catalyzed [$^{14}$C]-oleic acid formation. 0.05 µCi/mL of [1-$^{14}$C]-eicosatrienoic acid or [1-$^{14}$C]-linolenic acid plus 10 µM of 2-amino-N-(3-chlorophenyl)benzamide (a delta-5 desaturase inhibitor) was used to index the delta-5 and delta-6 desaturase activities, respectively. After 4 h incubation at 37° C., the culture media was removed and the labeled cells were washed with PBS (3×1 mL) at room temperature. The labeled cellular lipids were hydrolyzed under nitrogen at 65° C. for 1 h using 400 µL of 2N sodium hydroxide plus 50 µL of L-α-phosphatidylcholine (2 mg/mL in isopropanol, Sigma #P-3556). After acidification with phosphoric acid (60 µL), the radioactive species were extracted with 300 µL of acetonitrile and quantified on a HPLC that was equipped with a C-18 reverse phase column and a Packard Flow Scintillation Analyzer. The levels of [$^{14}$C]-oleic acid over [$^{14}$C]-stearic acid, [$^{14}$C]-arachidonic acid over [$^{14}$C]-eicosatrienoic acid, and [$^{14}$C]-eicosatetraenoic acid (8, 11, 14, 17) over [$^{14}$C]-linolenic acid were used as the corresponding activity indices of SCD, delta-5 and delta-6 desaturase, respectively.

The SCD inhibitors of formula I, particularly the inhibitors of Examples 1 to 20, exhibit an inhibition constant $IC_{50}$ of less than 1 µM and more typically less than 0.1 µM. Generally, the $IC_{50}$ ratio for delta-5 or delta-6 desaturases to SCD for a compound of formula I, particularly for Examples 1 to 20, is at least about ten or more, and preferably about one hundred or more.

In Vivo Efficacy of Compounds of the Present Invention:

The in vivo efficacy of compounds of formula I was determined by following the conversion of [1-$^{14}$C]-stearic acid to [1-$^{14}$C]oleic acid in animals as exemplified below. Mice were dosed with a compound of formula I and one hour later the radioactive tracer, [1-$^{14}$C]-stearic acid, was dosed at 20 µCi/kg IV. At 3 h post dosing of the compound, the liver was harvested and then hydrolyzed in 10 N sodium hydroxide for 24 h at 80° C., to obtain the total liver fatty acid pool. After phosphoric acid acidification of the extract, the amount of [1-$^{14}$C]-stearic acid and [1-$^{14}$C]-oleic acid was quantified on a HPLC that was equipped with a C-18 reverse phase column and a Packard Flow Scintillation Analyzer.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of formula I, and either administered separately or in the same pharmaceutical composition, include, but are not limited to:

(a) dipeptidyl peptidase-IV (DPP-4) inhibitors;

(b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, Galida, TAK-559, PPARα agonists, such as fenofibric acid derivatives (gemfibrozil, clofibrate, fenofibrate and bezafibrate), and selective PPARγ modulators (SPPARγM's), such as disclosed in WO 02/060388, WO 02/08188, WO 2004/019869, WO 2004/020409, WO 2004/020408, and WO 2004/066963; (ii) biguanides, such as metformin hydrochloride; and (iii) protein tyrosine phosphatase-1B (PTP-1B) inhibitors;

(c) insulin or insulin mimetics, including rapid acting insulin, regular insulin, long acting insulin, complexed forms of insulin and the like, administered by any conventional route, such as subcutaneous, intradermal or intramuscular injection, oral, transdermal, intranasal, intrapulmonary, and the like;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists, such as those disclosed in WO 98/04528, WO 99/01423, WO 00/39088, and WO 00/69810;

(g) GLP-1, GLP-1 analogues or mimetics, and GLP-1 receptor agonists, such as exendin-4 (exenatide), liraglutide (NN-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) CETP inhibitors, such as torcetrapib, JTT-705, and compounds disclosed in WO2005/100298, WO2006/014357, and WO2006/014413, and (ix) phenolic anti-oxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, β3 adrenergic receptor agonists, melanocortin-receptor agonists, in particular melanocortin-4 receptor agonists, ghrelin antagonists, bombesin receptor agonists (such as bombesin receptor subtype-3 agonists), and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as diuretics, e.g., hydrochlorothiazide, furosemide, and the like; beta adrenergic blocking drugs, such as propranolol, metaprolol and the like; ACE inhibitors (such as enalapril, lisinopril, captopril, quinapril, and tandolapril); A-II receptor blockers (such as losartan, candesartan, irbesartan, valsartan, telmisartan, and eprosartan) and calcium channel blockers, such as amlodipine, diltiazem and verapamil;

(p) glucokinase activators (GKAs), such as those disclosed in WO 03/015774; WO 04/076420; and WO 04/081001;

(q) inhibitors of 11β-hydroxysteroid dehydrogenase type 1, such as those disclosed in U.S. Pat. No. 6,730,690; WO 03/104207; and WO 04/058741;

(r) inhibitors of fructose 1,6-bisphosphatase, such as those disclosed in U.S. Pat. Nos. 6,054,587; 6,110,903; 6,284,748; 6,399,782; and 6,489,476;

(s) acetyl CoA carboxylase-1 and/or -2 inhibitors;

(t) AMPK activators; and (u) agonists of GPR-119.

Dipeptidyl peptidase-IV inhibitors that can be combined with compounds of structural formula I include those disclosed in U.S. Pat. No. 6,699,871; WO 02/076450 (3 Oct. 2002); WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); WO 03/082817 (9 Oct. 2003); WO 03/000181 (3 Jan. 2003); WO 04/007468 (22 Jan. 2004); WO 04/032836 (24 Apr. 2004); WO 04/037169 (6 May 2004); and WO 04/043940 (27 May 2004). Specific DPP-IV inhibitor compounds include sitagliptin (MK-0431); vildagliptin (LAF 237); denagliptin; P93/01; saxagliptin (BMS 477118); RO0730699; MP513; alogliptin (SYR-322); ABT-279; PHX1149; GRC-8200; TS021; and pharmaceutically acceptable salt thereof.

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of antiobesity compounds that can be combined with compounds of structural formula I, see S. Chaki et al., "Recent advances in feeding suppressing agents: potential therapeutic strategy for the treatment of obesity," *Expert Opin. Ther. Patents,* 11: 1677-1692 (2001); D. Spanswick and K. Lee, "Emerging antiobesity drugs," *Expert Opin. Emerging Drugs*, 8: 217-237 (2003); and J. A. Fernandez-Lopez, et al., "Pharmacological Approaches for the Treatment of Obesity," *Drugs*, 62: 915-944 (2002).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

CB1 receptor antagonists or inverse agonists that can be combined with compounds of formula I include those disclosed in PCT Publication WO 03/007887; U.S. Pat. No. 5,624,941, such as rimonabant; U.S. Pat. No. 6,972,295, such as taranabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; U.S. Pat. No. 5,292,736; PCT Publication WO 03/086288; PCT Publication WO 03/087037; PCT Publication WO 04/048317; PCT Publication WO 03/007887; PCT Publication WO 03/063781; PCT Publication WO 03/075660; PCT Publication WO 03/077847; PCT Publication WO 03/082190; PCT Publication WO 03/082191; PCT Publication WO 03/087037; PCT Publication WO 03/086288; PCT Publication WO 04/012671; PCT Publication WO 04/029204; PCT Publication WO 04/040040; PCT Publication WO 01/64632; PCT Publication WO 01/64633; and PCT Publication WO 01/64634.

Melanocortin-4 receptor (MC4R) agonists useful in the present invention include, but are not limited to, those disclosed in U.S. Pat. No. 6,294,534, U.S. Pat. Nos. 6,350,760, 6,376,509, 6,410,548, 6,458,790, U.S. Pat. No. 6,472,398, U.S. Pat. No. 5,837,521, U.S. Pat. No. 6,699,873, which are hereby incorporated by reference in their entirety; in US Patent Application Publication Nos. US 2002/0004512, US2002/0019523, US2002/0137664, US2003/0236262, US2003/0225060, US2003/0092732, US2003/109556, US 2002/0177151, US 2002/187932, US 2003/0113263, which are hereby incorporated by reference in their entirety; and in WO 99/64002, WO 00/74679, WO 02/15909, WO 01/70708, WO 01/70337, WO 01/91752, WO 02/068387, WO 02/068388, WO 02/067869, WO 03/007949, WO 2004/024720, WO 2004/089307, WO 2004/078716, WO 2004/078717, WO 2004/037797, WO 01/58891, WO 02/070511, WO 02/079146, WO 03/009847, WO 03/057671, WO 03/068738, WO 03/092690, WO 02/059095, WO 02/059107, WO 02/059108, WO 02/059117, WO 02/085925, WO 03/004480, WO 03/009850, WO 03/013571, WO 03/031410, WO 03/053927, WO 03/061660, WO 03/066597, WO 03/094918, WO 03/099818, WO 04/037797, WO 04/048345, WO 02/018327, WO 02/080896, WO 02/081443, WO 03/066587, WO 03/066597, WO 03/099818, WO 02/062766, WO 03/000663, WO 03/000666, WO 03/003977, WO 03/040107, WO 03/040117, WO 03/040118, WO 03/013509, WO 03/057671, WO 02/079753, WO 02//092566, WO 03/-093234, WO 03/095474, and WO 03/104761.

One particular aspect of combination therapy concerns a method of treating a condition selected from the group consisting of hypercholesterolemia, atherosclerosis, low HDL levels, high LDL levels, hyperlipidemia, hypertriglyceridemia, and dyslipidemia, in a mammalian patient in need of such treatment comprising administering to the patient a therapeutically effective amount of a compound of structural formula I and an HMG-CoA reductase inhibitor.

More particularly, this aspect of combination therapy concerns a method of treating a condition selected from the group consisting of hypercholesterolemia, atherosclerosis, low HDL levels, high LDL levels, hyperlipidemia, hypertriglyceridemia and dyslipidemia in a mammalian patient in need of such treatment wherein the HMG-CoA reductase inhibitor is a statin selected from the group consisting of lovastatin, simvastatin, pravastatin, cerivastatin, fluvastatin, atorvastatin, and rosuvastatin.

In another aspect of the invention, a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions is disclosed comprising administering to a mammalian patient in need of such treatment a therapeutically effective amount of a compound of structural formula I and an HMG-CoA reductase inhibitor.

In another aspect of the invention, a method for delaying the onset or reducing the risk of developing atherosclerosis in a human patient in need of such treatment is disclosed comprising administering to said patient an effective amount of a compound of structural formula I and an HMG-CoA reductase inhibitor.

More particularly, a method for delaying the onset or reducing the risk of developing atherosclerosis in a human patient in need of such treatment is disclosed, wherein the HMG-CoA reductase inhibitor is a statin selected from the group consisting of: lovastatin, simvastatin, pravastatin, cerivastatin, fluvastatin, atorvastatin, and rosuvastatin.

In another aspect of the invention, a method for delaying the onset or reducing the risk of developing atherosclerosis in a human patient in need of such treatment is disclosed, wherein the HMG-Co A reductase inhibitor is a statin and further comprising administering a cholesterol absorption inhibitor.

More particularly, in another aspect of the invention, a method for delaying the onset or reducing the risk of developing atherosclerosis in a human patient in need of such treatment is disclosed, wherein the HMG-Co A reductase inhibitor is a statin and the cholesterol absorption inhibitor is ezetimibe.

In another aspect of the invention, a pharmaceutical composition is disclosed which comprises:
(1) a compound of structural formula I;
(2) one or more compounds selected from the group consisting of:
   (a) dipeptidyl peptidase-IV (DPP-4) inhibitors;
   (b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, Galida, TAK-559, PPARα agonists, such as fenofibric acid derivatives (gemfibrozil, clofibrate, fenofibrate and bezafibrate), and selective PPARγ modulators (SPPARγM's), such as disclosed in WO 02/060388, WO 02/08188, WO 2004/019869, WO 2004/020409, WO 2004/020408, and WO 2004/066963; (ii) biguanides, such as metformin hydrochloride; and (iii) protein tyrosine phosphatase-1B (PTP-1B) inhibitors;
   (c) insulin or insulin mimetics, including rapid acting insulin, regular insulin, long acting insulin, complexed forms of insulin and the like, administered by any conventional route, such as subcutaneous, intradermal or intramuscular injection, oral, transdermal, intranasal, intrapulmonary, and the like;
   (d) sulfonylureas and other insulin secretagogues, such as tolbutamide, glyburide, glipizide, glimepiride, and meglitinides, such as nateglinide and repaglinide;
   (e) α-glucosidase inhibitors (such as acarbose and miglitol);

(f) glucagon receptor antagonists, such as those disclosed in WO 98/04528, WO 99/01423, WO 00/39088, and WO 00/69810;

(g) GLP-1, GLP-1 analogues or mimetics, and GLP-1 receptor agonists, such as exendin-4 (exenatide), liraglutide (NN-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPAR$\alpha$ agonists such as fenofibric acid derivatives (gemfibrozil, clofibrate, fenofibrate and bezafibrate), (v) PPAR$\alpha$/$\gamma$ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) CETP inhibitors, such as torcetrapib, JTT-705, and compounds disclosed in WO2005/100298, WO2006/014357, and WO2006/014413, and (ix) phenolic anti-oxidants, such as probucol;

(k) PPAR$\delta$ agonists, such as those disclosed in WO 97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, $\beta_3$ adrenergic receptor agonists, melanocortin-receptor agonists, in particular melanocortin-4 receptor agonists, ghrelin antagonists, bombesin receptor agonists (such as bombesin receptor subtype-3 agonists), and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as diuretics, e.g., hydrochlorothiazide, furosemide, and the like; beta adrenergic blocking drugs, such as propranolol, metaprolol and the like; ACE inhibitors (such as enalapril, lisinopril, captopril, quinapril, and tandolapril); A-II receptor blockers (such as losartan, candesartan, irbesartan, valsartan, telmisartan, and eprosartan) and calcium channel blockers, such as amlodipine, diltiazem and verapamil;

(p) glucokinase activators (GKAs), such as those disclosed in WO 03/015774; WO 04/076420; and WO 04/081001;

(q) inhibitors of 11$\beta$-hydroxysteroid dehydrogenase type 1, such as those disclosed in U.S. Pat. No. 6,730,690; WO 03/104207; and WO 04/058741;

(r) inhibitors of fructose 1,6-bisphosphatase, such as those disclosed in U.S. Pat. Nos. 6,054,587; 6,110,903; 6,284,748; 6,399,782; and 6,489,476;

(s) acetyl CoA carboxylase-1 and/or -2 inhibitors;

(t) AMPK activators; and (u) agonists of GPR-119; and (3) a pharmaceutically acceptable carrier.

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of stearoyl-CoA delta-9 desaturase enzyme activity an appropriate dosage level will generally be about 0.01 to 500 mg per kg patient body weight per day which can be administered in single or multiple doses. Preferably, the dosage level will be about 0.1 to about, 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

List of Abbreviations:

| | |
|---|---|
| Alk = | alkyl |
| APCI = | atmospheric pressure chemical ionization |
| Ar = | aryl |
| Boc = | tert-butoxycarbonyl |
| br = | broad |
| t-BuONO = | t-butyl nitrite |
| d = | doublet |
| DBU = | 1,8-diazabicyclo[5.4.0]undec-7-ene |
| DDQ = | 2,3-dichloro-5,6-dicyano-1,4-benzoquinone |
| DMF = | N,N-dimethylformamide |
| DIBAL-H = | diisobutylaluminum hydride |
| DMSO = | dimethyl sulfoxide |
| ESI = | electrospray ionization |
| ESMS = | electrospray ion-mass spectroscopy |
| EtOAc = | ethyl acetate |
| HATU = | O-(7-azabenzotriazol-1-yl)-N,N,N',N'-tetramethyluronium hexafluorophosphate |
| HPLC = | high-performance liquid chromatography |
| m = | multiplet |
| min = | minutes |
| MeOH = | methyl alcohol |
| MS = | mass spectroscopy |
| NaHMDS = | sodium bis(trimethylsilyl)amide |
| NMP = | 1-methyl-2-pyrrolidinone |
| NMR = | nuclear magnetic resonance spectroscopy |
| PG = | protecting group |
| rt or RT = | room temperature |
| s = | singlet |
| t = | triplet |
| TFAA = | trifluoroacetic anhydride |
| Tf$_2$O = | trifluoromethanesulfonic anhydride |
| THF = | tetrahydrofuran |
| TLC = | thin-layer chromatography |
| TsOH = | toluene-4-sulfonic acid |

Preparation of Compounds of the Invention:

The compounds of structural formula I can be prepared according to the procedures of the following Schemes and Examples, using appropriate materials and are further exemplified by the following specific examples. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Mass spectra (MS) were measured by electrospray ion-mass spectroscopy (ESMS).

Method A:

An appropriately substituted heteroaryl amine 1 is reacted with t-butyl nitrite and anhydrous copper (II) halide in a solvent such as acetonitrile to give halide 2. Treatment of 2 with concentrated ammonium hydroxide in a solvent such as THF gives amide 3. Dehydration with TFAA or Tf$_2$O in a solvent such as CH$_2$Cl$_2$ gives the nitrile intermediate 4.

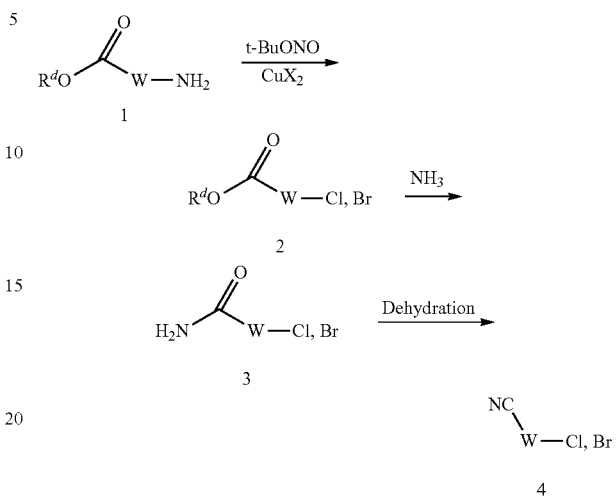

Method B:

An appropriately substituted halo-heteroaryl amine 5 is reacted with t-butyl nitrite and anhydrous cuprous cyanide in a solvent such as acetonitrile to give the nitrile intermediate 4.

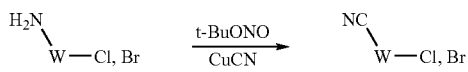

Method C:

The nitrile intermediate 4 is reacted with an appropriately substituted cyclic amine 6 in the presence of a base such as DBU or an alkali metal (K, Na, Cs) carbonate in a solvent such as THF, 1,4-dioxane, and DMF at a temperature range of room temperature to refluxing temperature. Extractive work-up and purification by flash column chromatography gives the coupled product 7.

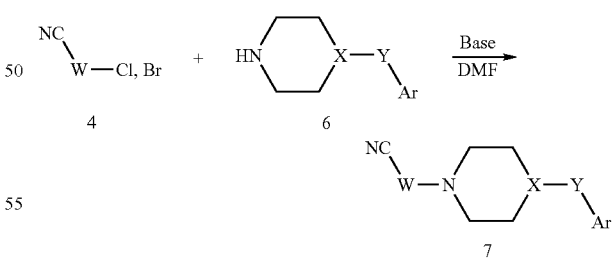

Method D:

The ester intermediate 2 is reacted with an appropriately substituted cyclic amine 6 in the presence of a base such as DBU or an alkali metal (K, Na, Cs) carbonate in a solvent such as THF, 1,4-dioxane, and DMF at a temperature range of room temperature to refluxing temperature. Extractive work-up and purification by flash column chromatography gives the coupled product 8. The ester group of 8 is hydrolyzed with an alkaline base such as NaOH in a solvent such as aqueous THF with an alcoholic solvent such as MeOH at room temperature to reflux temperature to give a carboxylic acid intermediate. The carboxylic acid is then converted to amide 9 via the corresponding acid chloride with $NH_3$ in a solvent such as THF or under direct amidation reaction as described by McMurray [*Tetrahedron Lett.*, 2501 (1999)] with $NH_4Cl$ in the presence of a coupling reagent such as HATU and a base such as N,N-diisopropylethylamine in a solvent such as DMF. Dehydration of amide 9 with TFAA or $Tf_2O$ in a solvent such as $CH_2Cl_2$ gives the nitrile 7.

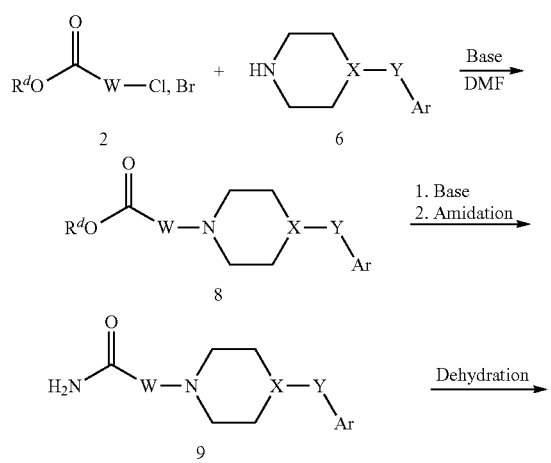

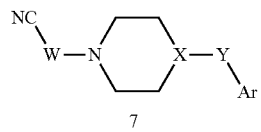

Method E:

The nitrile intermediate 7 prepared according to Method C or D is reacted with $NaN_3$ in the presence of a Lewis acid catalyst such as pyridine hydrochloride in a solvent such as NMP, or with $NaN_3$ in the presence of a Lewis acid catalyst such as $ZnBr_2$ in a solvent such as 2-propanol and water to give the tetrazole intermediate 10. Alkylation with a halo ester such as ethyl bromoacetate in the presence of a base such as $Cs_2CO_3$ or KOt-Bu in a solvent such as DMF usually gives a mixture of 11 and 12, which can be separated by flash column chromatography. Hydrolysis of the ester groups in 11 and 12 with an alkaline base, such as sodium hydroxide, in a solvent, such as THF, with an alcoholic solvent, such as MeOH, at a temperature range from room temperature to reflux temperature gives the carboxylic acids 14 and 15. Structures of 14 and 15 can be further confirmed by X-ray crystallography or $^{15}N$ gradient Heteronuclear Multiple Bond Correlation ($^{15}N$ gHMBC) NMR experiments.

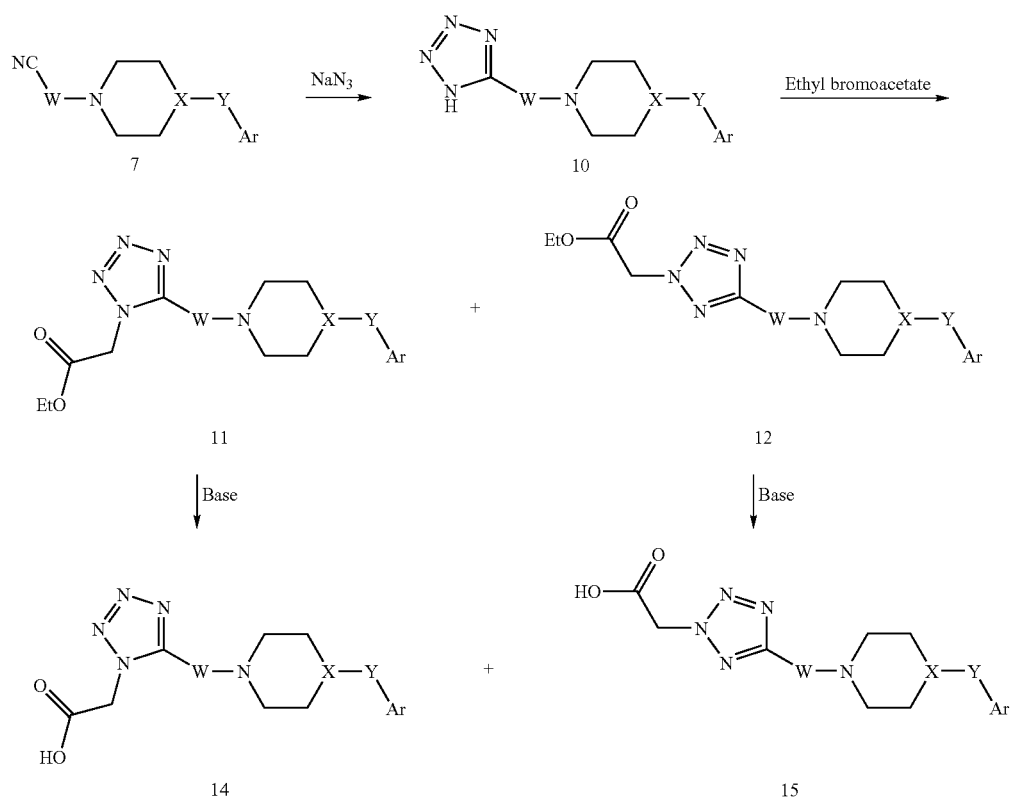

Method F:

The nitrile intermediate 7 prepared according to Method C or D is reacted with hydrogen sulfide in the presence of a base such as triethylamine or alkaline sodium ethoxide in a solvent such as 1,4-dioxane or ethanol to give the thioamide 16. The thioamide intermediate 16 is subsequently reacted with an alpha-halo keto ester such as methyl 4-chloroacetoacetate to give the ester intermediate 17. Hydrolysis of the ester group with an alkaline base such as sodium hydroxide in a solvent such as THF with an alcoholic solvent such as MeOH at a temperature range from room temperature to reflux temperature gives the carboxylic acid 18.

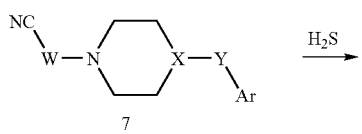

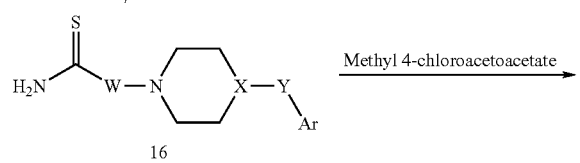

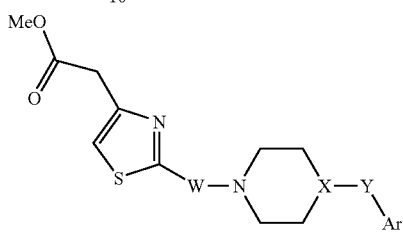

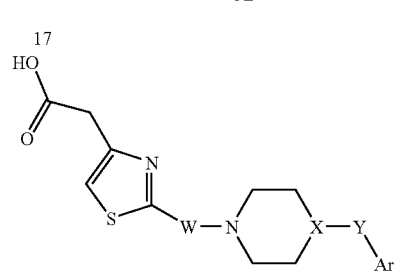

Method G:

Where W represents an isoxazole residue, a mixture of oxime 19 and an acrylate ester 20 is reacted in the presence of a base, such as potassium and sodium bicarbonat, in a solvent system such as EtOAc, THF, EtOAc-H$_2$O to give an ester intermediate, which is treated with ammonia in an alcoholic solvent or concentrated ammonium hydroxide in a solvent such as THF to give the bromo isoxazoline amide 21. Oxidation of 21 with iodine, in the presence of a base such as sodium acetate, DDQ, or MnO$_2$ in a solvent such as benzene, halobenzene and toluene at a temperature range from room temperature to reflux temperature gives the isoxazole intermediate 23. The isoxazole amide 23 is then converted to the tetrazole 24 via a corresponding nitrile intermediate according to suitable steps in Method D and E. The tetrazole 24 is then reacted with a bromoacetate ester in the presence of a base such as Et$_3$N, or an alkaline metal (K, Na, Cs) carbonate in a solvent such as THF, 1,4-dioxane or DMF at a temperature range from room temperature to refluxing temperature. The 2-alkylated ester tetrazole intermediate is usually obtained along with the 1-alkylated isomer that can be separated by chromatography. Hydrolysis of the ester group in the 2-alkylated ester tetrazole intermediate with an alkaline base, such as sodium hydroxide, in a solvent, such as THF, with an alcoholic solvent, such as MeOH, at a temperature range from room temperature to reflux temperature gives the carboxylic acid 25. When a tert-butyl ester is used, the ester group is cleaved with TFAA, in a solvent such as CH$_2$Cl$_2$, or an acid such as formic acid in water at a temperature range from room temperature to reflux temperature to give 25. The structure of 25 can be further confirmed by $^{15}$N gHMBC NMR experiments.

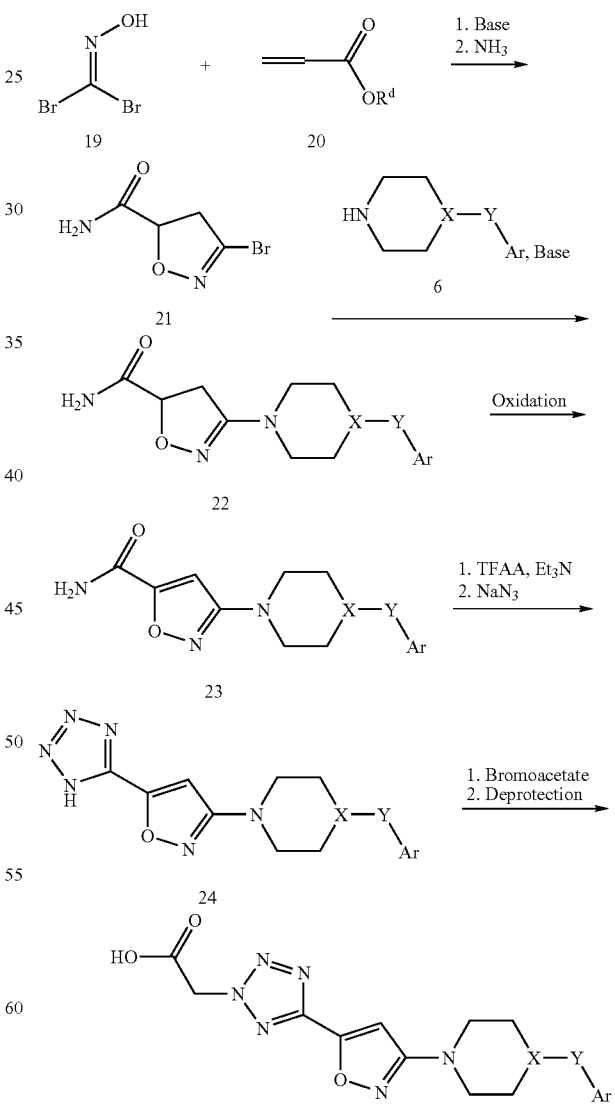

Method H:

An appropriately substituted cyclic amine 6 is reacted with cyanogen bromide in the presence of a base, such as triethylamine, in a solvent, such as THF to afford the cyanamide derivative 26. Reaction of cyanamide 26 with hydroxylamine hydrochloride in EtOH/water in the presence of a base such as sodium carbonate under reflux temperature condition gives the carboximidamide 27. Reaction of carboximidamide 27 with an appropriately substituted heteroaryl acid chloride 28 in the presence of a base, such as triethylamine and sodium hydride, in a solvent, such as THF, at room temperature or under reflux temperature condition affords the intermediate 29. Alkylation of the heteroaryl nitrogen with a halo ester, such as ethyl bromoacetate, in the presence of a base, such as triethylamine and sodium hydride, in a solvent, such as THF, gives the heteroaryl acetate intermediate. The ester group can be hydrolysed with aqueous NaOH in a solvent such as THF and MeOH at a temperature range from about room temperature to about refluxing temperature followed by extractive work up and purification by flash column chromatography or recrystallization to afford the final product 30.

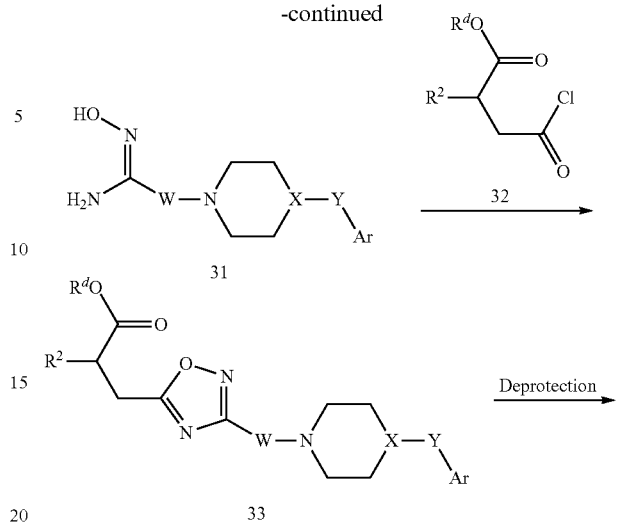

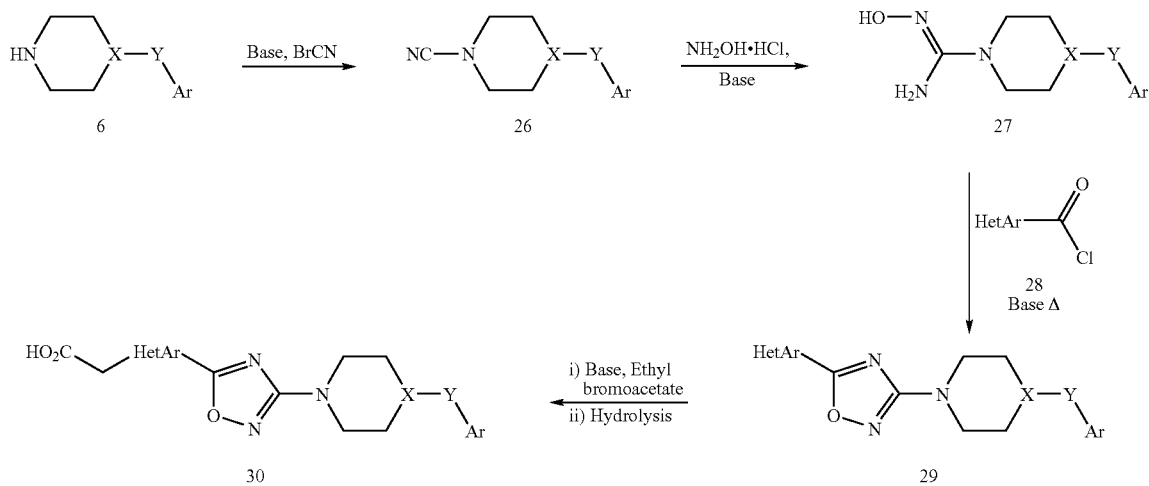

Method I:

The nitrile intermediate 7 prepared according to Method C or D is reacted with hydroxylamine hydrochloride in the presence of a base such as an alkaline metal (K, Na, Cs) carbonate in a solvent such as DMF, EtOH, THF, and 1,4-dioxane at a temperature range of room temperature to reflux temperature to give the carboximidamide 31. Reaction with an appropriate substituted carboxylic acid halide 32 in the presence of a base such as pyridine in a solvent such as $CH_2Cl_2$ gives an intermediate which is subsequently converted to 33 by refluxing in pyridine. Cleavage of the ester group in 33 by hydrolysis with as an alkali base (NaOH) in a solvent such as THF or with an alcoholic solvent such as MeOH gives final product 34.

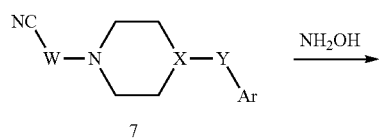

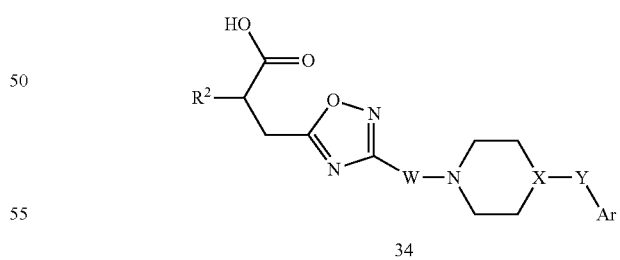

Method J:

The carboxylic acid 35 prepared according to Method E or G, wherein the phenyl ring bears a halogen group as indicated, is cross-coupled under Suzuki-type conditions with an arylboronic acid and a base such as aqueous $Na_2CO_3$ in the presence of a catalyst such as $Pd(Ph_3P)_4$ in a solvent such as toluene at an appropriate temperature to give the biaryl product 36.

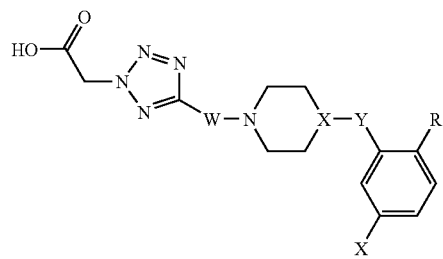 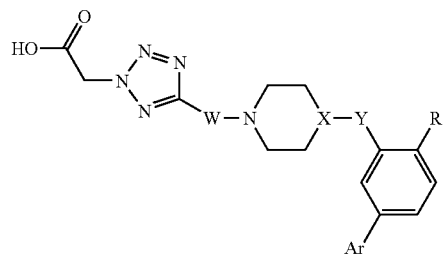

Suzuki cross coupling
Ar—B(OH)2
Base
"Pd"

X = Cl, Br, I

Preparation of Intermediates:

Intermediate 1

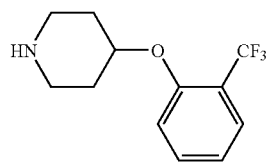

4-[2-(Trifluoromethyl)phenoxy]piperidine

To a solution of tert-butyl 4-hydroxypiperidine-1-carboxylate (25 g, 124 mmol), 2-hydroxy-benzotrifluoride (22 g, 136 mmol) and triphenylphosphine (39 g, 149 mmol) in THF was added diethyl azodicarboxylate (23.5 mL, 149 mmol) dropwise at 0° C. The mixture was then warmed to room temperature and stirred for 14 h. The mixture was concentrated and diluted with Et$_2$O, washed with 1 N NaOH and water and then dried over Na$_2$SO$_4$. The mixture was concentrated and diluted with Et$_2$O/hexanes (35:65). The precipitated phosphine oxide was filtered and the filtrate was concentrated. The residue was purified by column chromatography on silica gel (eluting with 35% Et$_2$O/hexanes) to give tert-butyl 4-[2-(trifluoromethyl)phenoxy]-piperidine-1-carboxylate as a solid.

Trifluoroacetic acid (26.3 mL, 342 mmol) was added to a solution of tert-butyl 4-[2-(trifluoromethyl)phenoxy]piperidine-1-carboxylate (29.5 g, 85 mmol) in CH$_2$Cl$_2$ (171 mL). The mixture was stirred at room temperature for 16 h. The solvent was removed by evaporation. The residue was diluted with EtOAc (200 mL), washed with 2 N NaOH (3×100 mL), brine, dried over Na$_2$SO$_4$, and evaporated to give the title compound as an oil.

Intermediate 2

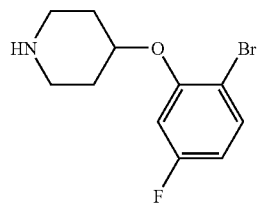

4-(2-Bromo-5-fluorophenoxy)piperidine

To a solution of tert-butyl 4-hydroxypiperidine-1-carboxylate (50.6 g, 251 mmol) and di-tert-butyl azodicarboxylate (71.0 g, 308 mmol) in THF (350 mL) was added 2-bromo-5-fluorophenol (36 mL, 324 mmol). The mixture was cooled to −78° C. and a solution of triphenylphosphine (81.5 g, 311 mmol) in CH$_2$Cl$_2$ (130 mL) was added via a cannula. The reaction was then warmed to room temperature and stirred overnight. The solvents were removed under vacuum and the crude oil was dissolved in EtOH (200 mL). The solution was cooled to −78° C. and treated with 4 M HCl in 1,4-dioxane (450 mL). The reaction was warmed to room temperature and stirred 24 h. After this time, the solvents were removed under vacuum. The salts were neutralized with 1 N NaOH (750 mL) and extracted with a mixture of Et$_2$O:hexanes (1:1) several times. The organic layers were combined and concentrated to dryness. The crude material was treated with heptane (1 L) and a white precipitate was filtered and discarded. The heptane layer was diluted with Et$_2$O and treated with 4 M HCl in 1,4-dioxane (100 mL). The resulting precipitate was collected by filtration and washed three times with Et$_2$O:hexanes (1:1). The salts were again neutralized with 1 N NaOH (500 mL) and extracted with a mixture of Et$_2$O:hexanes (1:1) several times. The organic layers were combined, washed with brine, dried (MgSO$_4$), filtered and concentrated. The crude material was dissolved in heptane (2 L), washed four times with 1 N NaOH (250 mL), brine and dried (MgSO$_4$). The organic layer was filtered and concentrated to dryness to afford the title product as a colorless oil.

$^1$H NMR (500 MHz, acetone-d$_6$): δ7.58 (dd, 1H), 7.00 (dd, 1H), 6.70 (td, 1H), 4.64-4.58 (m, 1H), 3.12-3.06 (m, 2H), 2.73-2.66 (m, 2H), 2.02-1.94 (m, 2H), 1.69-1.60 (m, 2H).

Intermediate 3

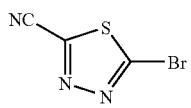

5-Bromo-1,3,4-thiadiazole-2-carbonitrile

Step 1: Ethyl 5-bromo-1,3,4-thiadiazole-2-carboxylate

To a suspension of ethyl 5-amino-1,3,4-thiadiazole-2-carboxylate (10 g, 58 mmol) in CH$_3$CN (180 mL) was added CuBr$_2$ (25.7 g, 115 mmol). The mixture turned dark green and was further stirred for 15 min at room temperature. t-BuONO, 90% (13.8 mL, 115 mmol) was added dropwise over 15-20 min. The mixture became slightly warm and gas was evolved after 5 min and then throughout the addition. After completion of the addition and gas evolution subsided, the mixture was heated at 60° C. for 30 min. Solvent was then evaporated in vacuo. Water and EtOAc were added and the mixture was agitated in the flask until the dark green color disappeared. The organic phase became light brown and the aqueous was green with insoluble material. The whole mixture was filtered through celite and washed with EtOAc. The EtOAc layer was separated, washed with dilute brine solution, dried (Na$_2$SO$_4$) and concentrated to give the title compound. $^1$H NMR (400 MHz, acetone-d$_6$): δ4.52 (q, 2H), 1.43 (t, 3H).

Step 2: 5-Bromo-1,3,4-thiadiazole-2-carboxamide

To a solution of ethyl 5-bromo-1,3,4-thiadiazole-2-carboxylate (13.5 g, 56.9 mmol) in THF (50 mL) at room temperature was added NH$_4$OH (28 wt. %, 39.6 mL, 164 mmol). The mixture was stirred at room temperature overnight and a precipitate appeared in the aqueous layer. Volatile materials were removed in vacuo. The mixture was diluted with water and the precipitate was collected, washed with water and dried under vacuum to give the title compound. $^1$H NMR (400 MHz, acetone-d$_6$): δ7.99 (s, 1H), 7.55 (s, 1H).

Step 3: 5-Bromo-1,3,4-thiadiazole-2-carbonitrile

To a solution of 5-bromo-1,3,4-thiadiazole-2-carboxamide (11 g, 53 mmol) and Et$_3$N (17.1 mL, 122 mmol) in THF (106 mL) at 0° C. was added TFAA (17 mL, 58 mmol). The mixture was then warmed to room temperature and stirred for 30 min. Solvent was evaporated in vacuo. The residue was diluted with water. The precipitate was collected, washed with water and dried to give the title compound. $^{13}$C NMR (300 MHz, CDCl$_3$): δ77.3, 109.0, 141.7.

The following Examples are provided to illustrate the invention and are not to be construed as limiting the scope of the invention in any manner.

Example 1

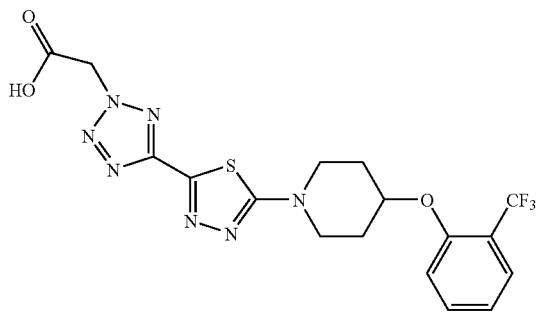

[5-(5-{4-[2-(Trifluoromethyl)phenoxy]piperidin-1-yl}-1,3,4-thiadiazol-2-yl)-2H-tetrazol-2-yl]acetic acid Step 1: 5-{4-[2-(Trifluoromethyl)phenoxy]piperidin-1-yl}-1,3,4-thiadiazol-2-amine To a solution of 4-[2-(trifluoromethyl)phenoxy]piperidine hydrochloride (5.5 g, 2.2 mmol) in DMF (50 mL) was added 5-bromo-1,3,4-thiadiazol-2-amine (3.3 g, 2.2 mmol) and K$_2$CO$_3$ (9.1 g, 6.6 mmol). The reaction was heated at 80° C. with stirring overnight. After cooling, the salt was removed by filtration and the filtrate was evaporated in vacuo. The residue was triturated with EtOAc to afford the title compound.
$^1$H NMR (400 MHz, DMSO-d$_6$): δ7.57-7.60 (m, 2H), 7.29-7.35 (m, 1H), 7.03-7.05 (m, 1H), 6.46 (s, 2H), 4.84 (s, 1H), 3.22-3.30 (m, 4H), 1.91-2.01 (m, 2H), 1.68-1.78 (m, 2H). MS: m/z 345 (MH$^+$).

Step 2: 5-{4-[2-(Trifluoromethyl)phenoxy]piperidin-1-yl}-1,3,4-thiadiazole-2-carbonitrile To a suspension of 5-{4-[2-(trifluoromethyl)phenoxy]piperidin-1-yl}-1,3,4-thiadiazol-2-amine (10.0 g, 29.0 mmol) in CH$_3$CN (150 mL) was added CuCN (5.3 g, 59.2 mmol) and t-BuONO (90%) (8 mL, 60.0 mmol) at room temperature. The reaction mixture was heated at 50-60° C. for 2 h until TLC indicated disappearance of the starting material. The reaction mixture was poured into water and CH$_2$Cl$_2$ was added. The solid was removed by filtration and the filtrate was extracted with CH$_2$Cl$_2$, dried (Na$_2$SO$_4$) and filtered. Solvents were removed in vacuo to afford the crude product, which was purified by column chromatography on silica gel (eluting with 5:1 petroleum ether/EtOAc) to afford the title compound. $^1$H NMR (400 MHz, CDCl$_3$): δ7.61 (d, 1H), 7.50 (t, 1H), 6.93-7.06 (m, 2H), 4.86 (br s, 1H), 3.77-3.83 (m, 4H), 2.01-2.20 (m, 4H). MS: m/z 355 (MH$^+$).

Step 3: 1-[5-(2H-Tetrazol-5-yl)-1,3,4-thiadiazol-2-yl]-4-[2-(trifluoromethyl)phenoxy]piperidine A suspension of 5-{4-[2-(trifluoromethyl)phenoxy]piperidin-1-yl}-1,3,4-thiadiazole-2-carbonitrile (4.99 g, 14.1 mmol), NaN$_3$ (4.65 g, 71.5 mmol) and pyridinium hydrochloride (3.43 g, 29.7 mmol) in NMP (50 mL) was heated at 130° C. for 18 h. The reaction mixture was cooled to room temperature and poured into aqueous 0.5 N HCl, extracted with EtOAc, washed three times with aqueous 0.5 N HCl, and with aqueous brine solution. The organic layer was dried (Na$_2$SO$_4$) and filtered. Evaporation of the solvent was followed by trituration in a mixture of MeOH/Et$_2$O/heptane (1:1:6) (v/v) with stirring for 4 h at room temperature. After this time, the suspension was cooled with an ice-water bath and the title compound was collected by filtration as a white solid. The material was dried under high vacuum by heating at 50° C. for 1-2 h.
$^1$H NMR (300 MHz, DMSO-d$_6$): δ7.60-7.62 (m, 2H), 7.37 (d, 1H), 7.08 (t, 1H), 4.86-4.95 (m, 1H), 3.56-3.64 (m, 4H), 2.00-2.15 (m, 2H), 1.75-1.89 (m, 2H). MS: m/z 398 (MH$^+$).

Step 4: Ethyl [5-(5-{4-[2-(trifluoromethyl)phenoxy]piperidin-1-yl}-1,3,4-thiadiazol-2-yl)-2H-tetrazol-2-yl]acetate and ethyl [5-(5-{4-[2-(trifluoromethyl)phenoxy]-piperidin-1-yl}-1,3,4-thiadiazol-2-yl)-1H-tetrazol-1-yl]acetate A solution of 1-[5-(2H-tetrazol-5-yl)-1,3,4-thiadiazol-2-yl]-4-[2-(trifluoromethyl)phenoxy]piperidine (262 mg, 0.66 mmol) in DMF (5 mL) was treated with NaH (60% in oil) (42 mg, 1.05 mmol) at −78° C. The mixture was warmed to 0° C. and, after 10 min, ethyl bromoacetate (150 μL, 1.35 mmol) was added dropwise. The final reaction mixture was warmed and stirred at room temperature until TLC indicated disappearance of the starting material. The reaction mixture was poured into aqueous 1 N HCl, extracted with EtOAc and washed with brine. The organic layer was dried (Na$_2$SO$_4$) and filtered. Solvents were removed in vacuo to afford the crude product, which was purified by column chromatography on silica gel (eluting with 10-50% EtOAc/hexanes) to afford ethyl [5-(5-{4-[2-(trifluoromethyl)phenoxy]piperidin-1-yl}-1,3,4-thiadiazol-2-yl)-2H-tetrazol-2-yl]acetate as the more polar regioisomer, $R_f$=0.2 (50% EtOAc/hexanes). $^1$H NMR (400 MHz, acetone-$d_6$): δ7.70-7.61 (m, 2H), 7.40 (d, 1H), 7.14 (t, 1H), 5.81 (s, 2H), 5.10-5.04 (m, 1H), 4.31 (q, 2H), 3.94-3.85 (m, 2H), 3.86-3.77 (m, 2H), 2.29-2.20 (m, 2H), 2.11-2.03 (dd, 2H), 1.31 (t, 3H).

Ethyl [5-(5-{4-[2-(trifluoromethyl)phenoxy]piperidin-1-yl}-1,3,4-thiadiazol-2-yl)-1H-tetrazol-1-yl]acetate was obtained as the less polar regioisomer, ($R_f$=0.3 (50% EtOAc/hexanes)).

$^1$H NMR (400 MHz, acetone-$d_6$): δ7.70-7.61 (m, 2H), 7.40 (d, 1H), 7.14 (t, 1H), 5.79 (s, 2H), 5.11-5.05 (m, 1H), 4.27 (q, 2H), 3.98-3.82 (m, 4H), 2.30-2.21 (m, 2H), 2.13-2.03 (m, 2H), 1.28 (t, 3H).

Step 5: [5-(5-{4-[2-(Trifluoromethyl)phenoxy]piperidin-1-yl}-1,3,4-thiadiazol-2-yl)-2H-tetrazol-2-yl]acetic acid A solution of ethyl [5-(5-{4-[2-(trifluoromethyl)phenoxy]piperidin-1-yl}-1,3,4-thiadiazol-2-yl)-2H-tetrazol-2-yl]acetate (134 mg, 0.28 mmol) in THF/MeOH (2:1) (v/v) (4.6 mL) was treated with aqueous 1 N NaOH (1.5 mL). The reaction mixture was stirred at room temperature until TLC indicated disappearance of the starting material. The reaction mixture was poured into aqueous aqueous 0.5 N HCl, extracted with EtOAc, washed with brine. The organic layer was dried (Na$_2$SO$_4$) and filtered. Evaporation of the solvent was followed by trituration in a mixture of Et$_2$O/heptane with stirring for 1 h at room temperature. After this time, the title compound was collected by filtration as a white solid.

$^1$H NMR (500 MHz, DMSO-$d_6$): δ13.67 (br s, 1H), 7.67-7.62 (m, 2H), 7.41 (d, 1H), 7.12 (t, 1H), 5.67 (s, 2H), 5.02-4.94 (m, 1H), 3.80-3.70 (m, 4H), 2.15-2.09 (m, 2H), 1.91-1.84 (m, 2H). MS: m/z 456.1 (MH$^+$).

Example 2

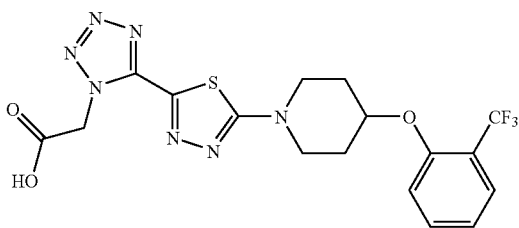

[5-(5-{4-[2-(Trifluoromethyl)phenoxy]piperidin-1-yl}-1,3,4-thiadiazol-2-yl)-1-H-tetrazol-1-yl]acetic acid The title compound was prepared in a similar manner as described in Example 1, Step 5 from the less polar regioisomer, ethyl [5-(5-{4-[2-(trifluoromethyl)phenoxy]piperidin-1-yl}-1,3,4-thiadiazol-2-yl)-1H-tetrazol-1-yl]acetate, obtained in Example 1, step 4.

$^1$H NMR (500 MHz, DMSO-$d_6$): δ13.91 (br s, 1H), 7.67-7.62 (m, 2H), 7.41 (d, 1H), 7.12 (t, 1H), 5.80 (s, 2H), 5.01-4.94 (m, 1H), 3.78-3.67 (m, 4H), 2.15-2.09 (m, 2H), 1.91-1.84 (m, 2H). MS: m/z 456.1 (MH$^+$).

Example 3

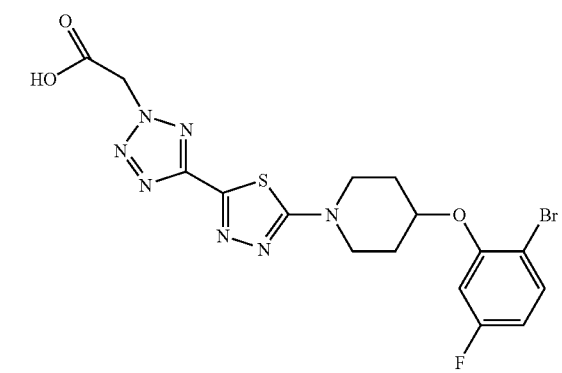

(5-{5-[4-(2-Bromo-5-fluorophenoxy)piperidin-1-yl]-1,3,4-thiadiazol-2-yl}-2H-tetrazol-2-yl)acetic acid Step 1: 5-[4-(2-Bromo-5-fluorophenoxy)piperidin-1-yl]-1,3,4-thiadiazole-2-carbonitrile To a solution of 4-(2-bromo-5-fluorophenoxy)piperidine (15.16 g, 52.5 mmol) in 1,4-dioxane (80 mL) was added N,N-diisopropylethylamine (Hünig's base or DIPEA) (20 mL, 115 mmol) followed by 5-bromo-1,3,4-thiadiazole-2-carbonitrile (10.02 g, 52.7 mmol). The mixture was stirred 1 h at room temperature. The reaction mixture was then poured into saturated aqueous NH$_4$Cl, extracted with EtOAc, washed with brine, dried (Na$_2$SO$_4$), filtered and concentrated under reduced pressure. The crude material was purified by column chromatography on silica gel (eluting with 10-40% EtOAc/hexanes) to afford the desired product as a colorless oil.

$^1$H NMR (500 MHz, acetone-$d_6$): δ7.63 (dd, 1H), 7.14 (dd, 1H), 6.78 (td, 1H), 5.04-4.99 (m, 1H), 4.00-3.95 (m, 2H), 3.89-3.84 (m, 2H), 2.27-2.21 (m, 2H), 2.11-2.05 (m, 2H).

Step 2: 4-(2-Bromo-5-fluorophenoxy)-1-[5-(2H-tetrazol-5-yl)-1,3,4-thiadiazol-2-yl]piperidine The title compound was prepared in a similar manner as described in Example 1, Step 3, with 5-[4-(2-bromo-5-fluorophenoxy)piperidin-1-yl]-1,3,4-thiadiazole-2-carbonitrile (15.6 g), NaN$_3$ (13.2 g, 204 mmol) and pyridinium hydrochloride (9.47 g, 82.0 mmol) in NMP (70 mL), and purification by trituration with a mixture of MeOH/Et$_2$O/heptane to afford the desired product as a white solid.

$^1$H NMR (400 MHz, acetone-$d_6$): δ7.64 (dd, 1H), 7.16 (dd, 1H), 6.79 (td, 1H), 5.04-5.00 (m, 1H), 4.02-3.94 (m, 2H), 3.89-3.81 (m, 2H), 2.29-2.20 (m, 2H), 2.12-2.03 (m, 2H). MS: m/z 428.0, 426.0 (MH$^+$).

Step 3: Ethyl (5-{5-[4-(2-bromo-5-fluorophenoxy)piperidin-1-yl]-1,3,4-thiadiazol-2-yl}-2H-tetrazol-2-yl)acetate and ethyl (5-{5-[4-(2-bromo-5-fluorophenoxy)piperidin-1-yl]-1,3,4-thiadiazol-2-yl}-1H-tetrazol-1-yl)acetate The title compounds were prepared in a similar manner as described in Example 1, Step 4, with 4-(2-bromo-5-fluorophenoxy)-1-[5-(2H-tetrazol-5-yl)-1,3,4-thiadiazol-2-yl]piperidine (4.54 g, 10.66 mmol), NaH (60% in oil) (512 mg, 12.80 mmol) and ethyl bromoacetate (1.6 mL, 14.37 mmol) in DMF (20 mL), and purification by column chromatography on silica gel (eluting with 10-50% EtOAc/hexanes). The more polar isomer (Rf=0.3 (50% EtOAc/hexanes)) was ethyl (5-{5-[4-(2-bromo-5-fluorophenoxy)piperidin-1-yl]-1,3,4-thiadiazol-2-yl}-2H-tetrazol-2-yl)acetate.

$^1$H NMR (500 MHz, DMSO-d$_6$): δ7.64 (dd, 1H), 7.29 (dd, 1H), 6.82 (td, 1H), 5.98 (s, 2H), 4.93-4.89 (m, 1H), 4.24 (q, 2H), 3.84-3.77 (m, 2H), 3.72-3.66 (m, 2H), 2.13-2.06 (m, 2H), 1.90-1.83 (m, 2H), 1.24 (t, 3H).

The less polar isomer (Rf=0.5 (50% EtOAc/hexanes)) was ethyl (5-{5-[4-(2-bromo-5-fluorophenoxy)piperidin-1-yl]-1,3,4-thiadiazol-2-yl}-1H-tetrazol-1-yl)acetate.

$^1$H NMR (500 MHz, DMSO-d$_6$): δ7.64 (dd, 1H), 7.29 (dd, 1H), 6.82 (td, 1H), 5.79 (s, 2H), 4.94-4.89 (m, 1H), 4.19 (q, 2H), 3.86-3.80 (m, 2H), 3.75-3.69 (m, 2H), 2.12-2.06 (m, 2H), 1.90-1.84 (m, 2H), 1.20 (t, 3H).

Step 4: (5-{5-[4-(2-Bromo-5-fluorophenoxy)piperidin-1-yl]-1,3,4-thiadiazol-2-yl}-2H-tetrazol-2-yl)acetic acid The title compound was prepared in a similar manner as described in Example 1, Step 5, with ethyl (5-{5-[4-(2-bromo-5-fluorophenoxy)piperidin-1-yl]-1,3,4-thiadiazol-2-yl}-2H-tetrazol-2-yl)acetate (2.57 g) and 1 N NaOH (10 mL) in THF/MeOH (30 mL) (v/v) (0.1 M), and purification by trituration in a mixture of Et$_2$O/heptane to give the desired material as a white solid. $^1$H NMR (400 MHz, DMSO-d$_6$): δ13.89 (br s, 1H), 7.65 (dd, 1H), 7.30 (dd, 1H), 6.83 (td, 1H), 5.84 (s, 2H), 4.95-4.88 (m, 1H), 3.86-3.78 (m, 2H), 3.74-3.66 (m, 2H), 2.15-2.07 (m, 2H), 1.92-1.84 (m, 2H). MS: m/z 485.8, 483.8 (MH$^+$).

Example 4

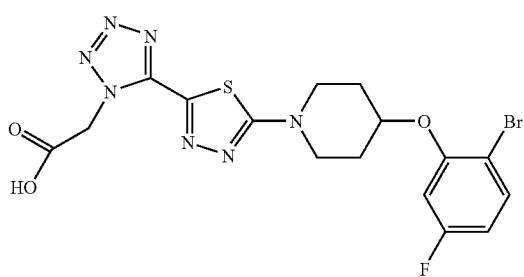

(5-{5-[4-(2-Bromo-5-fluorophenoxy)piperidin-1-yl]-1,3,4-thiadiazol-2-yl}-1H-tetrazol-1-yl)acetic acid The title compound was prepared in a similar manner as described in Example 1, Step 5, from the less polar regioisomer, ethyl (5-{5-[4-(2-bromo-5-fluorophenoxy)piperidin-1-yl]-1,3,4-thiadiazol-2-yl}-1H-tetrazol-1-yl)acetate, obtained in Example 3, Step 3.

$^1$H NMR (400 MHz, DMSO-d$_6$): δ13.68 (br s, 1H), 7.65 (dd, 1H), 7.30 (dd, 1H), 6.83 (td, 1H), 5.68 (s, 2H), 4.98-4.87 (m, 1H), 3.88-3.80 (m, 2H), 3.77-3.69 (m, 2H), 2.15-2.07 (m, 2H), 1.93-1.83 (m, 2H). MS: m/z 486.0, 484.0 (MH$^+$).

Example 5

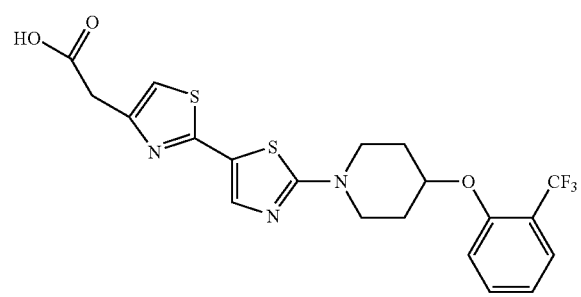

(2'-{4-[2-(Trifluoromethyl)phenoxy]piperidin-1-yl}-2,5'-bi-1,3-thiazol-4-yl)acetic acid Step 1: Methyl 2-{4-[2-(trifluoromethyl)phenoxy]piperidin-1-yl}-1,3-thiazole-5-carboxylate A mixture of methyl 2-bromo-1,3-thiazole-5-carboxylate (10 g, 45 mmol) and 4-[2-(trifluoromethyl)phenoxy]piperidine (12.1 g, 50 mmol) in dioxane (160 mL) was heated at 80-85° C. overnight. After cooling, the mixture was diluted with water and extracted with EtOAc. The EtOAc extract was washed twice with water, dried (Na$_2$SO$_4$) and concentrated. The crude material was purified by column chromatography on silica gel (eluting with 50% EtOAc/hexanes) to afford the title compound as a pale yellow oil.

$^1$H NMR (500 MHz, CDCl$_3$): δ7.90 (s, 1H), 7.62 (d, 1H), 7.51 (t, 1H), 7.06-7.02 (m, 2H), 4.82 (d, 1H), 3.85 (s, 3H), 3.80-3.70 (m, 4H), 2.12-2.02 (m, 4H).

Step 2: 2-{4-[2-(Trifluoromethyl)phenoxy]piperidin-1-yl}-1,3-thiazole-5-carboxylic acid A mixture of methyl 2-{4-[2-(trifluoromethyl)phenoxy]piperidin-1-yl}-1,3-thiazole-5-carboxylate (16 g, 41.4 mmol) and 1 N NaOH (85 mL, 85 mmol) in THF/MeOH (1:1) (v/v) (300 mL) was heated at 80° C. bath for 1 h. Volatile solvents were removed in vacuo. The residue was diluted with H$_2$O, acidified with 1 N HCl (2.2 equiv) and extracted with EtOAc. The EtOAc extract was washed with H$_2$O, dried (Na$_2$SO$_4$) and concentrated to give the title compound as a white solid.

$^1$H NMR (400 MHz, acetone-d$_6$): δ7.83 (s, 1H), 7.69-7.60 (m, 2H), 7.39 (d, 1H), 7.13 (t, 1H), 5.07-5.01 (m, 1H), 3.86-3.72 (m, 4H), 2.22-2.13 (m, 2H), 2.06-1.96 (m, 2H).

Step 3: 2-{4-[2-(Trifluoromethyl)phenoxy]piperidin-1-yl}-1,3-thiazole-5-carboxamide To a solution of 2-{4-[2-(trifluoromethyl)phenoxy]piperidin-1-yl}-1,3-thiazole-5-carboxylic acid (14.5 g, 39 mmol), HOBt (5.3 g, 39 mmol)), HATU (23.7 g, 62 mmol) and NH$_4$Cl (6.3 g, 117 mmol) in DMF (200 mL) at room temperature was added Hünig's base (34 mL, 195 mmol) over about 15 min. The mixture was stirred at room temperature overnight. After dilution with water, the mixture was extracted twice with EtOAc. The EtOAc extracts were combined, washed with 0.5 N NaOH (2×), diluted brine (1×), dried (Na₂SO₄) and concentrated. The residue was triturated with Et₂O/hexanes (1:1) to give the title compound as a pale yellow solid. ¹H NMR (500 MHz, acetone-d₆): δ7.79 (s, 1H), 7.67-7.61 (m, 2H), 7.38 (d, 1H), 7.12 (t, 1H), 5.02 (s, 1H), 3.76 (t, 2H), 3.71-3.67 (m, 2H), 2.16 (t, 2H), 2.00-1.94 (m, 2H).

Step 4: 2-{4-[2-(Trifluoromethyl)phenoxy]piperidin-1-yl}-1,3-thiazole-5-carbonitrile A suspension of 2-{4-[2-(trifluoromethyl)phenoxy]piperidin-1-yl}-1,3-thiazole-5-carboxamide (4 g, 10.8 mmol) in CH₂Cl₂ (100 mL) was cooled with an ice-acetone bath. Tf₂O (2.0 mL, 11.9 mmol) was then added dropwise over about 10 min. The mixture was stirred for 5 min and then the cooling bath was removed. After further stirring at room temperature for 15 min, the mixture was quenched with water and extracted twice with CH₂Cl₂. The combined CH₂Cl₂ extracts were washed twice with diluted brine, dried (Na₂SO₄) and concentrated. The crude material was purified by column chromatography on silica gel (eluting with 40% EtOAc/hexanes) to give the title compound as a pale yellow solid.
¹H NMR (400 MHz, acetone-d₆): δ7.88 (s, 1H), 7.69-7.60 (m, 2H), 7.39 (d, 1H), 7.14 (t, 1H), 5.09-5.03 (m, 1H), 3.87-3.75 (m, 4H), 2.24-2.15 (m, 2H), 2.06-1.98 (m, 2H).

Step 5: 2-{4-[2-(Trifluoromethyl)phenoxy]piperidin-1-yl}-1,3-thiazole-5-carbothioamide To a solution of 2-{4-[2-(trifluoromethyl)phenoxy]piperidin-1-yl}-1,3-thiazole-5-carbonitrile (354 mg, 1.0 mmol) in dioxane was added Et₃N (20 μL, 0.14 mmol) and H₂S (gas) was bubbled through the solution for about 1 min. After stirring at room temperature for 3 h, ethanol was added, followed by 21 wt. % NaOEt in ethanol (238 μL, 0.6 mmol). More H₂S (gas) was bubbled through the solution for another minute. The mixture was then stirred at room temperature for 3 days. Volatile materials were removed in vacuo. The residue was dissolved in EtOAc, washed twice with water, dried (Na₂SO₄) and concentrated. Trituration with Et₂O gave the title compound as a pale yellow solid.
¹H NMR (400 MHz, acetone-d₆): δ8.52 (s, 1H), 8.32 (s, 1H), 7.82 (s, 1H), 7.69-7.60 (m, 2H), 7.39 (d, 1H), 7.13 (t, 1H), 5.04 (t, 1H), 3.84-3.69 (m, 4H), 2.21-2.12 (m, 2H), 2.05-1.95 (m, 2H). MS (+ESI) m/z 388 (MH⁺).

Step 6: Methyl (2'-{4-[2-(trifluoromethyl)phenoxy]piperidin-1-yl}-2,5'-bi-1,3-thiazol-4-yl)acetate A mixture of 2-{4-[2-(trifluoromethyl)phenoxy]piperidin-1-yl}-1,3-thiazole-5-carbothioamide (240 mg, 0.62 mmol) and methyl 4-chloroacetoacetate (73 μL, 0.62 mmol) in methanol (3 mL) was heated in a sealed tube at 80-85° C. overnight. After cooling, the mixture was diluted with water and extracted with EtOAc. The EtOAc extract was washed twice with water, dried (Na₂SO₄) and concentrated. The crude material was purified by column chromatography on silica gel (eluting with 30-60% EtOAc/hexanes) to give the title compound as a pale yellow gum.
¹H NMR (400 MHz, acetone-d₆): δ7.72 (s, 1H), 7.69-7.60 (m, 2H), 7.39 (d, 1H), 7.26 (s, 1H), 7.13 (t, 1H), 5.06-5.00 (m, 1H), 3.86-3.67 (m, 9H), 2.23-2.14 (m, 2H), 2.06-1.95 (m, 2H). MS (+ESI) m/z 484 (MH⁺).

Step 7: (2'-{4-[2-(Trifluoromethyl)phenoxy]piperidin-1-yl}-2,5'-bi-1,3-thiazol-4-yl)acetic acid A mixture of methyl (2'-{4-[2-(trifluoromethyl)phenoxy]piperidin-1-yl}-2,5'-bi-1,3-thiazol-4-yl)acetate (220 mg, 0.44 mmol) in THF/MeOH (4:1) (v/v) (5 mL) was treated with 1 N NaOH (1 mL, 1 mmol) and heated at reflux temperature for 2 h. Volatile materials were removed in vacuo. The residue was diluted with water, acidified with 1 N HCl and extracted with EtOAc. The EtOAc extract was washed twice with water, dried (Na₂SO₄) and concentrated to give the title compound as a yellow foam.
¹H NMR (400 MHz, acetone-d₆): δ10.93 (s, 1H), 7.72 (s, 1H), 7.69-7.61 (m, 2H), 7.39 (d, 1H), 7.28 (s, 1H), 7.13 (t, 1H), 5.07-5.01 (m, 1H), 3.85-3.68 (m, 6H), 2.23-2.14 (m, 2H), 2.06-1.96 (m, 2H). MS (+ESI) m/z 470 (MH⁺).

Example 6

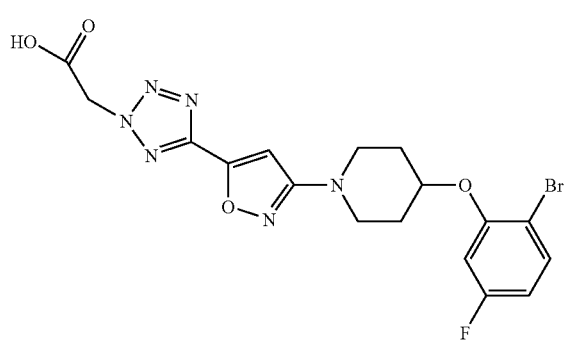

(5-{3-[4-(2-Bromo-5-fluorophenoxy)piperidin-1-yl]isoxazol-5-yl}-2H-tetrazol-2-yl)acetic acid Step 1: Ethyl 3-bromo-4,5-dihydroisoxazole-5-carboxylate To a vigorously stirred mixture of hydroxycarbonimidic dibromide (15.5 g, 76.4 mmol) and ethyl acrylate (15.3 g, 153 mmol) in DMF (200 mL) was added a solution of 15 wt % aqueous KHCO₃ (102 mL, 153 mmol). The mixture was stirred at room temperature overnight. Water was added and the mixture was extracted twice with methyl tert-butyl ether. The combined extracts were washed with brine, dried (Na₂SO₄) and concentrated in vacuo to give the title compound.

Step 2: 3-Bromo-4,5-dihydroisoxazole-5-carboxamide

A mixture of ethyl 3-bromo-4,5-dihydroisoxazole-5-carboxylate (6.2 g, 28 mmol) and a solution of 2M ammonia in MeOH (56 mL) was stirred at room temperature for 1-2 h. Volatile materials were removed in vacuo to give the crude title compound as a white solid.

Step 3: 3-[4-(2-Bromo-5-fluorophenoxy)piperidin-1-yl]-4,5-dihydroisoxazole-5-carboxamide A mixture of 3-bromo-4,5-dihydroisoxazole-5-carboxamide (1.5 g, 7.77 mmol), 4-(2-bromo-5-fluorophenoxy)piperidine (2.56 g, 9.33 mmol) and N,N-diisopropylethylamine (3.5 mL, 20.04 mmol) in ethanol (15 mL) was heated at reflux temperature overnight. Solvent was then removed in vacuo. The residue was suspended in water and stirred for 1 h. The solid was collected, washed with water and Et₂O. Drying under vacuum gave the title compound as a light brown powder.

¹H NMR (500 MHz, acetone-d₆): δ7.61 (dd, 1H), 7.07 (dd, 1H), 7.02 (s, 1H), 6.74 (td, 1H), 6.63 (s, 1H), 4.85-4.78 (m, 2H), 3.56-3.50 (m, 2H), 3.40-3.23 (m, 4H), 2.10-1.05 (m, 2H), 1.89-1.82 (m, 2H).

Step 4: 3-[4-(2-Bromo-5-fluorophenoxy)piperidin-1-yl]isoxazole-5-carboxamide

To a stirred suspension of 3-[4-(2-bromo-5-fluorophenoxy)piperidin-1-yl]-4,5-dihydroisoxazole-5-carboxamide (2.3 g, 5.96 mmol) and sodium acetate (1.3 g, 15.85 mmol) in chlorobenzene (15 mL) was added iodine (2 g, 7.88 mmol). The mixture was heated at reflux temperature for 3 h. After cooling, a solution of Na₂S₂O₃, water and EtOAc were added. The mixture was stirred for 5 min and filtered through celite to remove the insoluble material. The organic layer was then separated, washed with brine, dried (Na₂SO₄) and concentrated. The residue was triturated with Et₂O to give the title compound as light brown powder.

¹H NMR (500 MHz, acetone-d₆) δ7.61 (m, 1H), 7.51 (s, 1H), 7.10 (dd, 2H), 6.78 (s, 1H), 6.75 (td, 1H), 4.89-4.84 (m, 1H), 3.67-3.60 (m, 2H), 3.45-3.38 (m, 2H), 2.16-2.08 (m, 2H), 1.98-1.88 (m, 2H).

Step 5: 3-[4-(2-Bromo-5-fluorophenoxy)piperidin-1-yl]isoxazole-5-carbonitrile

To a suspension of 3-[4-(2-bromo-5-fluorophenoxy)piperidin-1-yl]isoxazole-5-carboxamide (1.6 g, 4.2 mmol) and Et₃N (1.5 mL, 10.8 mmol) in CH₂Cl₂ (20 mL) was added TFAA (0.8 mL, 5.7 mmol) at ice-water bath temperature. A homogeneous solution resulted. After addition, the cooling bath was removed and the mixture was stirred at room temperature for 2 h. The mixture was quenched with water (10-15 mL), followed by saturated aqueous NaHCO₃ (15-20 mL) and extracted with CH₂Cl₂ (2×30 mL). The combined CH₂Cl₂ extracts were washed with diluted brine (40 mL), dried (Na₂SO₄) and concentrated. Chromatography over silica gel and elution with hexanes:EtOAc (4:1) gave the title compound as a colorless gum.

¹H NMR (400 MHz, acetone-d₆): δ7.62 (dd, 1H), 7.33 (s, 1H), 7.10 (dd, 1H), 6.76 (td, 1H), 4.93-4.86 (m, 1H), 3.71-3.63 (m, 2H), 3.52-3.44 (m, 2H), 2.18-2.09 (m, 2H), 1.99-1.90 (m, 2H).

Step 6: 4-(2-Bromo-5-fluorophenoxy)-1-[5-(1H-tetrazol-5-yl)isoxazol-3-yl]piperidine A mixture of 3-[4-(2-bromo-5-fluorophenoxy)piperidin-1-yl]isoxazole-5-carbonitrile (1.4 g, 3.82 mmol), pyridinium hydrochloride (0.9 g, 7.79 mmol) and sodium azide (1.3 g, 20.00 mmol) in NMP (12 mL) was stirred and heated at 130° C. bath for 2 h. After cooling, the mixture was diluted with water and acidified with 1N HCl (some precipitate appeared). The whole mixture was then extracted with EtOAc. The EtOAc extract was washed with water (3×), dried (Na₂SO₄) and concentrated. The residue was triturated with diethyl ether to give the title compound as a light brown powder.

¹H NMR (400 MHz, acetone-d₆): δ7.63 (dd, 1H), 7.12 (m, 2H), 6.76 (td, 1H), 4.93-4.88 (m, 1H), 3.77-3.69 (m, 2H), 3.55-3.47 (m, 2H), 2.21-2.13 (m, 2H), 2.02-1.92 (m, 2H).

Step 7: Ethyl (5-{3-[4-(2-Bromo-5-fluorophenoxy)piperidin-1-yl]isoxazol-5-yl}-2H-tetrazol-2-yl)acetate A mixture of 4-(2-bromo-5-fluorophenoxy)-1-[5-(1H-tetrazol-5-yl)isoxazol-3-yl]piperidine (1.2 g, 2.93 mmol), ethyl bromoacetate (0.45 mL, 4.04 mmol) and triethylamine (0.75 mL, 5.38 mmol) in THF (12 mL) was heated at reflux temperature for 2 h. After cooling, the mixture was diluted with water and extracted with EtOAc. The EtOAc extract was washed with water, dried (Na₂SO₄) and concentrated. Combi-Flash chromatography (40 g, 25-40% EtOAc in hexanes for 20 min, 35 mL/min, 18 mL/fraction) gave the title compound as a colorless gum, containing about 20% of 1-alkylated isomer.

¹H NMR (400 MHz, acetone-d₆): δ7.63 (dd, 1H), 7.14-7.09 (m, 1H), 7.03 (s, 1H), 6.76 (td, 1H), 5.84 (s, 2H), 4.93-4.87 (m, 1H), 4.34-4.26 (m, 2H), 3.77-3.68 (m, 2H), 3.55-3.46 (m, 2H), 2.21-2.12 (m, 2H), 2.03-1.91 (m, 2H), 1.30 (t, 3H).

Step 8: (5-{3-[4-(2-Bromo-5-fluorophenoxy)piperidin-1-yl]isoxazol-5-yl}-2H-tetrazol-2-yl)acetic acid To a solution of ethyl (5-{3-[4-(2-bromo-5-fluorophenoxy)piperidin-1-yl]isoxazol-5-yl}-2H-tetrazol-2-yl)acetate (1.3 g, 2.62 mmol) in THF (15 mL) and MeOH (5 mL) was added 1M sodium hydroxide (5.25 mL, 5.25 mmol). The mixture was stirred at room temperature for 1 h. Volatile solvents were removed in vacuo. The residue was diluted with water (20 mL), acidified with 1M HCl (6 mL) and extracted with EtOAc. The EtOAc extract was washed with water, dried (Na₂SO₄) and concentrated. The residue was triturated with diethyl ether to give the crude product, containing about 5% of the 1-isomer. Further purification by trituration in isopropyl acetate (2×, 80° C. overnight, then room temperature overnight) provided the title compound as a beige powder.

¹H NMR (400 MHz, DMSO-d₆): δ13.90 (s, 1H), 7.63 (dd, 1H), 7.29-7.24 (m, 2H), 6.81 (td, 1H), 5.86 (s, 2H), 4.84 (m, 1H), 3.63-3.55 (m, 2H), 3.43-3.33 (m, 2H), 2.06-2.00 (m, 2H), 1.78 (d, 2H). MS (+ESI) m/z 467, 469.

Example 7

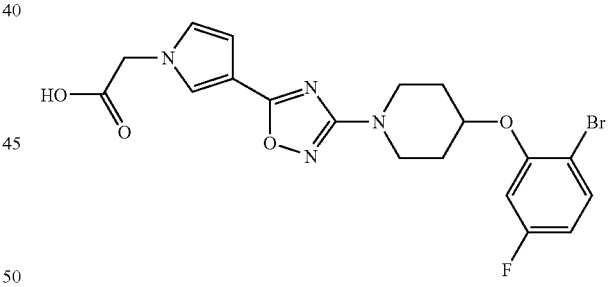

(3-{3-[4-(2-Bromo-5-fluorophenoxy)piperidin-1-yl]-1,2,4-oxadiazol-5-yl}-1H-pyrrol-1-yl)acetic acid Step 1: 4-(2-Bromo-5-fluorophenoxy)piperidine-1-carbonitrile To a solution of 4-(2-bromo-5-fluorophenoxy)piperidine (2.0 g, 7.30 mmol) in THF (24.3 ml) was added cyanogen bromide (0.77 g, 7.30 mmol) followed by triethylamine (1.01 ml, 7.3 mmol) at 0° C. The mixture was warmed to rt and further stirred for 1 h. Solvent was evaporated and the residue was diluted with 1N HCl (20 mL). The aqueous layer was extracted with EtOAc (3×10 mL). The combined organic fractions were washed with water (20 mL) and dried over Na₂SO₄. The solvent was evaporated under reduced pressure to afford the title compound as a solid which was used in the next step without further purification.

$^1$H NMR (500 MHz, acetone-$d_6$): δ7.62 (dd, 1H), 7.08 (dd, 1H), 6.76 (td, 1H), 4.88-4.84 (m, 1H), 3.55-3.48 (m, 2H), 3.32-3.25 (m, 2H), 2.16-2.09 (m, 2H), 1.99-1.91 (m, 2H).

Step 2: 4-(2-Bromo-5-fluorophenoxy)-N'-hydroxypiperidine-1-carboximidamide

A mixture of 4-(2-bromo-5-fluorophenoxy)piperidine-1-carbonitrile (1.6 g, 5.3 mmol), hydroxylamine hydrochloride (1.1 g, 16.1 mmol) and Na$_2$CO$_3$ (2.3 g, 92 mmol) in EtOH/water 4:1 (26 ml) was heated at 80° C. for 1 h. The solvent was evaporated. The residue was acidified with 6N HCl and washed with Et$_2$O (2×10 mL). The aqueous layer was made basic with solid Na$_2$CO$_3$ and extracted with EtOAc (3×20 mL). The combined organic fractions were dried over Na$_2$SO$_4$ and the solvent was evaporated under reduced pressure to give the title compound as a foam which was used in the next step without further purification. MS: m/z 332, 334 (MH$^+$).

Step 3: 4-(2-Bromo-5-fluorophenoxy)-1-[5-(1H-pyrrol-3-yl)-1,2,4-oxadiazol-3-yl]piperidine To a mixture of pyrrole-3-carboxylic acid hydrate (93 mg, 0.723 mmol) in THF (2007 μL) was added oxalyl chloride (264 μL, 3.01 mmol) followed by DMF (10 μL) at 0° C. The mixture was warmed to rt and stirred for 0.5 h. The solvent was evaporated, the residue diluted with THF (1 mL), evaporated again and dried under high vacuum. The residue was diluted with THF (2007 μL), 4-(2-bromo-5-fluorophenoxy)-N'-hydroxypiperidine-1-carboximidamide (200 mg, 0.602 mmol) was added followed by triethylamine (252 μL, 1.806 mmol). The mixture was stirred at rt for 0.5 h, then heated at 80° C. for 1 h. The mixture was cooled to RT and then sodium hydride (72.2 mg, 1.806 mmol) was added. The mixture was stirred at RT for 0.5 h and then heated at 80° C. for 1 h. The solvent was evaporated and the residue diluted with water (2 mL). The aqueous layer was extracted with EtOAc (3×2 mL). The combined organic fractions were dried over Na$_2$SO$_4$ and the solvent was evaporated. Purification by Combiflash chromatography (SiO$_2$-12 g, gradient elution of 30-60% EtOAc/hexanes over 25 min) afforded the title product. $^1$H NMR (500 MHz, acetone-$d_6$): δ7.61 (s, 2H), 7.11 (s, 1H), 6.99 (s, 1H), 6.75 (s, 1H), 6.65 (s, 1H), 4.89 (s, 1H), 3.76 (s, 2H), 3.54 (s, 2H), 1.99-1.82 (m, 2H), 2.10 (s, 2H). MS: m/z 407, 409 (MH$^+$).

Step 4: Ethyl (3-{3-[4-(2-bromo-5-fluorophenoxy)piperidin-1-yl]-1,2,4-oxadiazol-5-yl}-1H-pyrrol-1-yl)acetate To a solution of 4-(2-bromo-5-fluorophenoxy)-1-[5-(1H-pyrrol-3-yl)-1,2,4-oxadiazol-3-yl]piperidine (60 mg, 0.15 mmol) in DMF (491 μL) was added sodium hydride (11.8 mg, 0.3 mmol). After 5 min, ethyl bromoacetate (25 μL, 0.22 mmol) was added and the mixture was heated at 80° C. for 3 h. The mixture was poured onto ice cold 1N HCl (2 mL) and extracted with EtOAc (3×2 mL). The combined organic fractions were washed with water (2 mL) and then dried over Na$_2$SO$_4$. The solvent was evaporated. Purification by Combiflash chromatography (SiO$_2$-12 g, gradient elution of 30-60% EtOAc/hexanes over 25 min) gave the title compound.

$^1$H NMR (500 MHz, acetone-$d_6$): δ7.64-7.58 (m, 2H), 7.10 (dd, 1H), 6.95 (s, 1H), 6.75 (td, 1H), 6.62 (s, 1H), 5.03-4.92 (m, 2H), 4.88 (s, 1H), 4.33-4.10 (m, 2H), 3.80-3.72 (m, 2H), 3.56-3.49 (m, 2H), 2.17-2.06 (m, 2H), 1.91 (dd, 2H), 1.31-1.18 (m, 3H). MS: m/z 493, 495 (MH$^+$).

Step 5: (3-{3-[4-(2-Bromo-5-fluorophenoxy)piperidin-1-yl]-1,2,4-oxadiazol-5-yl}-1H-pyrrol-1-yl)acetic acid To a solution of ethyl (3-{3-[4-(2-bromo-5-fluorophenoxy)piperidin-1-yl]-1,2,4-oxadiazol-5-yl}-1H-pyrrol-1-yl)acetate (35 mg, 0.071 mmol) in THF (236 μL) and MeOH (118 μL) was added 1N NaOH (142 μL, 0.142 mmol). The mixture was stirred at RT for 10 min. The THF and MeOH were removed by evaporation under diminished pressure and the aqueous layer was washed with Et$_2$O (2×2 mL). The aqueous layer was acidified to pH 1 with 1N HCl and extracted with EtOAc (3×2 mL). The combined organic fractions were dried over Na$_2$SO$_4$ and the solvent was evaporated to afford the title compound.

$^1$H NMR (500 MHz, acetone-$d_6$): δ7.62-7.56 (m, 2H), 7.08 (dd, 1H), 6.94 (d, 1H), 6.72 (td, 1H), 6.58 (s, 1H), 4.96 (s, 2H), 4.87-4.83 (m, 1H), 3.76-3.69 (m, 2H), 3.53-3.47 (m, 2H), 2.11-2.05 (m, 2H), 1.92-1.84 (m, 2H). MS: m/z 465, 467 (MH$^+$).

Example 8

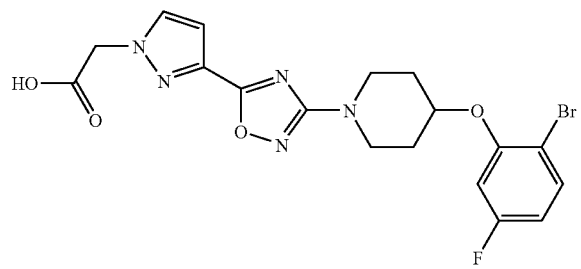

(3-{3-[4-(2-Bromo-5-fluorophenoxy)piperidin-1-yl]-1,2,4-oxadiazol-5-yl}-1-yl)acetic acid

Step 1: 4-(2-Bromo-5-fluorophenoxy)-1-[5-(1H-pyrazol-3-yl)-1,2,4-oxadiazol-3-yl]piperidine A mixture of 3-pyrazolecarboxylic acid (55.7 mg, 0.497 mmol) in thionyl chloride (989 μL, 13.55 mmol) was heated at 80° C. for 2 h. The excess thionyl chloride was removed by evaporation. The residue was diluted with THF (1 mL), evaporated and dried under high vacuum. The residue was dissolved in THF (1505 μL) and (2-bromo-5-fluorophenoxy)-N'-hydroxypiperidine-1-carboximidamide (150 mg, 0.452 mmol) was added, followed by triethylamine (189 μL, 1.355 mmol). The mixture was heated at 80° C. for 1 h. The solvent was evaporated and saturated NaHCO$_3$ (2 mL) was added. The aqueous layer was extracted with EtOAc (3×2 mL). The combined organic fractions were dried over Na$_2$SO$_4$ and the solvent was evaporated. Purification by Combiflash chromatography (SiO$_2$-12 g, gradient elution of 20-50% EtOAc/hexanes over 25 min) afforded the title product.

$^1$H NMR (500 MHz, acetone-$d_6$): δ12.90 (s, 1H), 7.98 (s, 1H), 7.62 (dd, 1H), 7.11 (dd, 1H), 6.95 (s, 1H), 6.82-6.72 (m, 1H), 4.92-4.88 (m, 1H), 3.83-3.76 (m, 2H), 3.64-3.55 (m, 2H), 2.17-2.11 (m, 2H), 1.98-1.90 (m, 2H). MS: m/z 408, 410 (MH$^+$).

Step 2: Ethyl (3-{3-[4-(2-bromo-5-fluorophenoxy)piperidin-1-yl]-1,2,4-oxadiazol-5-yl}-1H-pyrazol-1-yl)acetate The title compound was prepared in a similar manner as described in Example 7 (step 4) from 4-(2-bromo-5-fluorophenoxy)-1-[5-(1H-pyrazol-3-yl)-1,2,4-oxadiazol-3-yl]piperidine, sodium hydride and ethyl bromoacetate and obtained as the more polar isomer.
$^1$H NMR (500 MHz, acetone-d$_6$): δ7.69 (s, 1H), 7.62 (dd, 1H), 7.13-7.08 (m, 2H), 6.76 (td, 1H), 5.48 (s, 2H), 4.92 (t, 1H), 4.29-4.17 (m, 2H), 3.81-3.72 (m, 2H), 3.62-3.55 (m, 2H), 2.17-2.10 (m, 2H), 1.98-1.90 (m, 2H), 1.27-1.21 (m, 3H). MS: m/z 494, 496 (MH$^+$).

The less polar isomer isolated was ethyl (5-{3-[4-(2-bromo-5-fluorophenoxy)piperidin-1-yl]-1,2,4-oxadiazol-5-yl}-1H-pyrazol-1-yl)acetate. $^1$H NMR (500 MHz, acetone-d$_6$): δ7.69 (s, 1H), 7.62 (dd, 1H), 7.13-7.08 (m, 2H), 6.76 (td, 1H), 5.48 (s, 2H), 4.92 (t, 1H), 4.29-4.17 (m, 2H), 3.81-3.72 (m, 2H), 3.62-3.55 (m, 2H), 2.17-2.10 (m, 2H), 1.98-1.90 (m, 2H), 1.27-1.21 (m, 3H). MS: m/z 494, 496 (MH$^+$).

Step 3: (3-{3-[4-(2-Bromo-5-fluorophenoxy)piperidin-1-yl]-1,2,4-oxadiazol-5-yl}-1H-pyrazol-1-yl)acetic acid The title compound was prepared in a similar manner as described in Example 7 (step 5) from ethyl (3-{3-[4-(2-bromo-5-fluorophenoxy)piperidin-1-yl]-1,2,4-oxadiazol-5-yl}-1H-pyrazol-1-yl)acetate and aqueous NaOH. $^1$H NMR (500 MHz, acetone-d$_6$): δ 7.97 (s, 1H), 7.62 (t, 1H), 7.12 (d, 1H), 6.94 (s, 1H), 6.75 (s, 1H), 5.22 (s, 2H), 4.91 (s, 1H), 3.82-3.75 (m, 2H), 3.63-3.57 (m, 2H), 2.16-2.07 (m, 2H), 1.94 (s, 2H). MS: m/z 466, 468 (MH$^+$).

Example 9

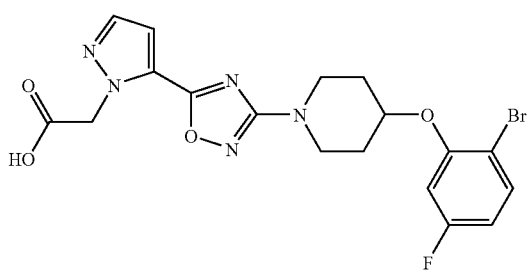

(5-{3-[4-(2-Bromo-5-fluorophenoxy)piperidin-1-yl]-1,2,4-oxadiazol-5-yl}-1H-pyrazol-1-yl)acetic acid The title compound was prepared in a similar manner as described in Example 7 (step 5) from ethyl (5-{3-[4-(2-bromo-5-fluorophenoxy)piperidin-1-yl]-1,2,4-oxadiazol-5-yl}-1H-pyrazol-1-yl)acetate and aqueous NaOH. $^1$H NMR (500 MHz, acetone-d$_6$): δ7.68 (d, 1H), 7.62 (dd, 1H), 7.14-7.08 (m, 2H), 6.76 (td, 1H), 5.49 (s, 2H), 4.93-4.89 (m, 1H), 3.81-3.74 (m, 2H), 3.66-3.55 (m, 2H), 2.16-2.10 (m, 2H), 1.98-1.88 (m, 2H). MS: m/z 466, 468 (MH$^+$).

Example 10

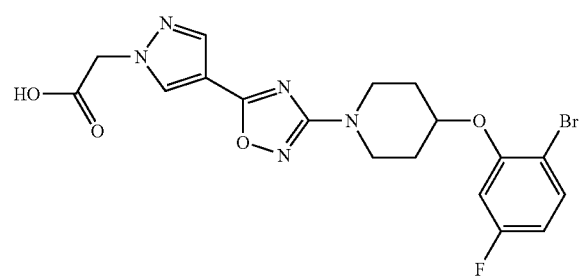

(4-{3-[4-(2-Bromo-5-fluorophenoxy)piperidin-1-yl]-1,2,4-oxadiazol-5-yl}-1H-pyrazol-1-yl)acetic acid Step 1: 4-(2-Bromo-5-fluorophenoxy)-1-[5-(1H-pyrazol-4-yl)-1,2,4-oxadiazol-3-yl]piperidine The title compound was prepared in a similar manner as described in Example 8 (step 1) from 4-pyrazolecarboxylic acid, thionyl chloride and (2-bromo-5-fluorophenoxy)-N'-hydroxypiperidine-1-carboximidamide. $^1$H NMR (500 MHz, acetone-d$_6$): δ12.82 (s, 1H), 8.48 (s, 1H), 8.11-7.96 (m, 1H), 7.62 (dd, 1H), 7.11 (dd, 1H), 6.75 (td, 1H), 4.92-4.88 (m, 1H), 3.80-3.73 (m, 2H), 3.59-3.52 (m, 2H), 2.17-2.11 (m, 2H), 1.98-1.88 (m, 2H). MS: m/z 408, 410 (MH$^+$).

Step 2: Ethyl (4-{3-[4-(2-bromo-5-fluorophenoxy)piperidin-1-yl]-1,2,4-oxadiazol-5-yl}-1H-pyrazol-1-yl)acetate The title compound was prepared in a similar manner as described in Example 7 (step 4) from 4-(2-bromo-5-fluorophenoxy)-1-[5-(1H-pyrazol-4-yl)-1,2,4-oxadiazol-3-yl]piperidine, sodium hydride and ethyl bromoacetate.
$^1$H NMR (500 MHz, acetone-d$_6$): δ8.47 (s, 1H), 8.04-7.99 (m, 1H), 7.62 (dd, 1H), 7.11 (dd, 1H), 6.75 (td, 1H), 5.19 (s, 2H), 4.92-4.88 (m, 1H), 4.30-4.19 (m, 2H), 3.80-3.70 (m, 2H), 3.59-3.52 (m, 2H), 2.15-2.09 (m, 2H), 1.96-1.88 (m, 2H), 1.27 (t, 3H). MS: m/z 494, 496 (MH$^+$).

Step 3: (4-{3-[4-(2-Bromo-5-fluorophenoxy)piperidin-1-yl]-1,2,4-oxadiazol-5-yl}-1H-pyrazol-1-yl)acetic acid The title compound was prepared in a similar manner as described in Example 7 (step 5) from ethyl (4-{3-[4-(2-bromo-5-fluorophenoxy)piperidin-1-yl]-1,2,4-oxadiazol-5-yl}-1H-pyrazol-1-yl)acetate and aqueous NaOH.
$^1$H NMR (500 MHz, acetone-d$_6$): δ8.48 (s, 1H), 8.03 (s, 1H), 7.62 (dd, 1H), 7.11 (dd, 1H), 6.75 (td, 1H), 5.20 (s, 2H), 4.90 (s, 1H), 3.80-3.74 (m, 2H), 3.59-3.52 (m, 2H), 2.15-2.08 (m, 2H), 1.95-1.89 (m, 2H). MS: m/z 466, 468 (MH$^+$).

Example 11

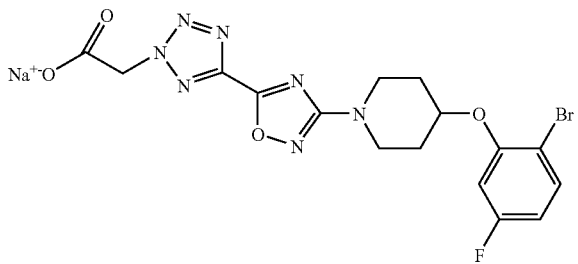

Sodium(5-{3-[4-(2-bromo-5-fluorophenoxy)piperidin-1-yl]-1,2,4-oxadiazol-5-yl}-2H-tetrazol-2-yl) acetate

Step 1: 3-[4-(2-Bromo-5-fluorophenoxy)piperidin-1-yl]-1,2,4-oxadiazole-5-carboxamide To a solution of (2-bromo-5-fluorophenoxy)-N'-hydroxypiperidine-1-carboximidamide (14.5 g, 43.7 mmol) and pyridine (10.59 mL, 131 mmol) in THF (146 ml) was added methyl oxalyl chloride (8.91 mL, 96 mmol) at 0° C. The mixture was warmed to RT and stirred for 1 h. The solvent was evaporated and the residue was diluted with 1N HCl (200 mL). The aqueous layer was extracted with EtOAc (3×200 mL). The combined organic fractions were washed with brine (200 mL), dried over $Na_2SO_4$ and the solvent was evaporated under reduced pressure. Purification by Combiflash chromatography ($SiO_2$-300 g, gradient elution of 80-100% EtOAc/hexanes over 40 min) afforded methyl 3-[4-(2-bromo-5-fluorophenoxy)piperidin-1-yl]-1,2,4-oxadiazole-5-carboxylate as the less polar compound and methyl (6E)-7-[4-(2-bromo-5-fluorophenoxy)piperidin-1-yl]-3,4,9-trioxo-2,5-dioxa-6,8-diazadec-6-en-10-oate as the more polar compound. These two compounds were combined and dissolved in MeOH (146 mL), cooled to 0° C. and ammonia gas was bubbled through for 5 min and stirred at 0° C. for 15 min. The mixture was then warmed to RT and further stirred for 4 h. The mixture was diluted with $Et_2O$ (100 mL). The solid was filtered and washed with $Et_2O$. The filtrate was evaporated and dried in vacuo. The crude product was filtered through silica gel and eluted with 2:1 EtOAc/hexanes. Evaporation of the solvent afforded the title compound. MS: m/z 585, 587 ($MH^+$).

Step 2: 3-[4-(2-Bromo-5-fluorophenoxy)piperidin-1-yl]-1,2,4-oxadiazole-5-carbonitrile To a solution of 3-[4-(2-bromo-5-fluorophenoxy)piperidin-1-yl]-1,2,4-oxadiazole-5-carboxamide (11 g, 28.6 mmol) and triethylamine (12.74 ml, 91 mmol) in THF (95 ml) was added trifluoroacetic anhydride (6.05 mL, 42.8 mmol) dropwise at 0° C. The mixture was warmed to RT and stirred for a further 30 min. The solvent was evaporated and the residue was diluted with $Et_2O$ (50 mL) then with dilute $NaHCO_3$ solution (100 mL). The aqueous layer was extracted with $Et_2O$ (3×100 mL). The combined organic fractions were dried over $Na_2SO_4$ and the solvent was evaporated under reduced pressure. Purification by Combiflash chromatography ($SiO_2$-120 g, gradient elution of 10-30% EtOAc/hexanes over 25 min) afforded the title compound.

$^1H$ NMR (500 MHz, acetone-$d_6$): δ7.62 (dd, 1H), 7.11 (dd, 1H), 6.76 (td, 1H), 4.95-4.90 (m, 1H), 3.80-3.73 (m, 2H), 3.62 (ddd, 2H), 2.17-2.10 (m, 2H), 1.98-1.91 (m, 2H).

Step 3: 4-(2-Bromo-5-fluorophenoxy)-1-[5-(1H-tetrazol-5-yl)-1,2,4-oxadiazol-3-yl]piperidine A mixture of 3-[4-(2-bromo-5-fluorophenoxy)piperidin-1-yl]-1,2,4-oxadiazole-5-carbonitrile (8 g, 21.79 mmol), sodium azide (2.125 g, 32.7 mmol) and ammonium chloride (5.83 g, 109 mmol) in DMF (43.6 ml) was heated at 100° C. for 0.5 h. The mixture was cooled to RT, diluted with 1N NaOH (50 mL), washed with $Et_2O$ (2×50 mL). The aqueous layer was acidified to pH about 1 with 2N HCl and extracted with EtOAc (3×75 mL). The combined organic fractions were washed with water (2×50 mL) then dried over $Na_2SO_4$. The solvent was evaporated under reduced pressure, the product dissolved in a small amount of EtOAc and precipitated with hexanes. The solid was filtered and washed with hexanes to afford the title compound. MS: m/z 410, 412 ($MH^+$).

Step 4: Ethyl (5-{5-[4-(2-bromo-5-fluorophenoxy) piperidin-1-yl]-1,2,4-oxadiazol-3-yl}-2H-tetrazol-2-yl)acetate To a solution of 4-(2-bromo-5-fluorophenoxy)-1-[5-(1H-tetrazol-5-yl)-1,2,4-oxadiazol-3-yl]piperidine (2 g, 4.88 mmol) in DMF (16.25 ml) was added sodium hydride (0.390 g, 9.75 mmol). After 5 min, ethyl bromoacetate (1.352 ml, 12.19 mmoles) was added and the mixture was heated at 80° C. for 0.5 h. The reaction mixture was cooled to RT, then poured over ice-cold 0.5 N HCl (100 mL) and extracted with EtOAc (3×25 mL). The combined organic fractions were washed with water (50 mL) and then dried over $Na_2SO_4$. The solvent was evaporated under reduced pressure. Purification by Combiflash chromatography ($SiO_2$-120 g, gradient elution of 0-10% $Et_2O/CHCl_3$ over 25 min) afforded the title product as the less polar isomer.

$^1H$ NMR (500 MHz, acetone-$d_6$): δ7.63 (dd, 1H), 7.13 (dd, 1H), 6.76 (td, 1H), 5.92 (s, 2H), 4.97-4.92 (m, 1H), 4.31 (q, 2H), 3.88-3.78 (m, 2H), 3.70-3.62 (m, 2H), 2.21-2.13 (m, 2H), 2.01-1.93 (m, 2H), 1.31 (t, 3H).

The more polar isomer isolated was ethyl (5-{5-[4-(2-bromo-5-fluorophenoxy)piperidin-1-yl]-1,2,4-oxadiazol-3-yl}-1H-tetrazol-2-yl)acetate.

$^1H$ NMR (500 MHz, acetone-$d_6$): δ7.63 (dd, 1H), 7.12 (dd, 1H), 6.77 (td, 1H), 5.87 (s, 2H), 4.97-4.93 (m, 1H), 4.29 (q, 2H), 3.85-3.77 (m, 2H), 3.69-3.62 (m, 2H), 2.19-2.12 (m, 2H), 2.01-1.93 (m, 2H), 1.30-1.24 (m, 3H).

Step 5: Sodium(5-{3-[4-(2-bromo-5-fluorophenoxy) piperidin-1-yl]-1,2,4-oxadiazol-5-yl}-2H-tetrazol-2-yl)acetate To a solution of ethyl (5-{5-[4-(2-bromo-5-fluorophenoxy)piperidin-1-yl]-1,2,4-oxadiazol-3-yl}-2H-tetrazol-2-yl)acetate (1.65 g, 3.32 mmol) in THF (11.08 ml) and MeOH (5.54 ml) was added 1N NaOH (3.32 ml, 3.32 mmol) and the mixture stirred at RT for 10 min. The THF and MeOH were evaporated and the aqueous layer diluted with water (2 mL) and washed with $Et_2O$ (2×10 mL). The aqueous layer was lyophilized to afford the title compound.

$^1H$ NMR (500 MHz, DMSO-$d_6$): δ7.63 (dd, 1H), 7.27 (dd, 1H), 6.80 (td, 1H), 5.07 (s, 2H), 4.89-4.84 (m, 1H), 3.74-3.66

(m, 2H), 3.57-3.50 (m, 2H), 2.07-2.00 (m, 2H), 1.83-1.77 (m, 2H). MS: m/z 468, 470 (MH+).

Example 12

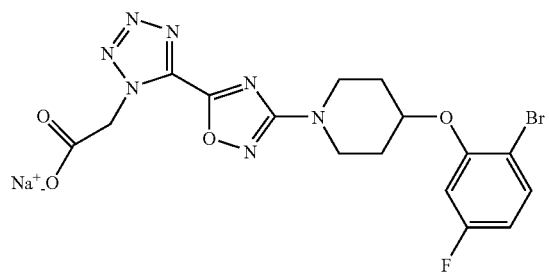

The title compound was prepared in a similar manner as described in Example 11 (step 5) from ethyl (5-{5-[4-(2-bromo-5-fluorophenoxy)piperidin-1-yl]-1,2,4-oxadiazol-3-yl}-1H-tetrazol-2-yl)acetate from Example 11 (step 4) and 1N NaOH.

$^1$H NMR (500 MHz, DMSO-$d_6$): δ7.66-7.58 (m, 1H), 7.27 (dd, 1H), 6.82-6.75 (m, 1H), 5.05 (s, 2H), 4.87 (s, 1H), 3.71-3.63 (m, 2H), 3.55-3.48 (m, 2H), 2.04 (d, 2H), 1.80 (d, 2H). MS: m/z 468, 470 (MH+).

Example 13

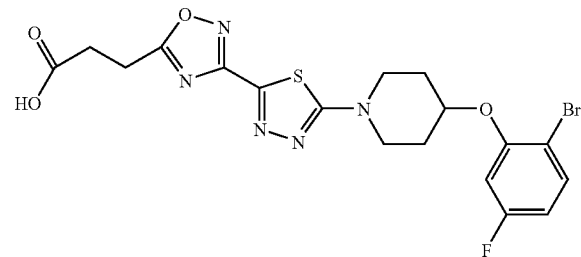

3-(3-{5-[4-(2-Bromo-5-fluorophenoxy)piperidin-1-yl]-1,3,4-thiadiazol-2-yl}-1,2,4-oxadiazol-5-yl)propanoic acid Step 1: 5-[4-(2-Bromo-5-fluorophenoxy)piperidin-1-yl]-N'-hydroxy-1,3,4-thiadiazole-2-carboximidamide The title compound was prepared in a similar manner as described for Example 7, step 2 from 5-[4-(2-bromo-5-fluorophenoxy)piperidin-1-yl]-1,3,4-thiadiazole-2-carbonitrile and hydroxylamine hydrochloride.

Step 2: Ethyl 3-(3-{5-[4-(2-bromo-5-fluorophenoxy)piperidin-1-yl]-1,3,4-thiadiazol-2-yl}-1,2,4-oxadiazol-5-yl)propanoate 5-[4-(2-Bromo-5-fluorophenoxy)piperidin-1-yl]-N'-hydroxy-1,3,4-thiadiazole-2-carboximidamide (500 mg, 1.2 mmol) was dissolved in CH$_2$Cl$_2$ (5 mL) and cooled to 0° C. in an ice-water bath. To this solution was added pyridine (0.155 mL, 1.92 mmol) followed by ethyl 3-chloro-3-oxopropanoate (270 mg, 1.8 mmol). After stirring for 1 h, the solvent was removed in vacuo. The residue was dissolved in pyridine (8 mL) and stirred at 90° C. overnight. The solvent was removed and the residue was partitioned between EtOAc and water. The combined organic layers were dried over anhydrous Na$_2$SO$_4$, filtered and evaporated in vacuo. The crude product was purified by preparative TLC to afford the title compound.

$^1$H NMR (400 MHz, CDCl$_3$): δ7.48-7.52 (m, 1H), 6.61-6.70 (m, 2H), 4.70-4.72 (m, 1H), 4.14-4.19 (m, 2H), 3.78-3.92 (m, 4H), 3.28 (t, 2H), 2.96 (t, 2H), 2.03-2.10 (m, 4H), 1.24-1.27 (m, 3H).

Step 3: 3-(3-{5-[4-(2-Bromo-5-fluorophenoxy)piperidin-1-yl]-1,3,4-thiadiazol-2-yl}-1,2,4-oxadiazol-5-yl)propanoic acid The title compound was prepared in a similar manner as described in Example 7 (step 5) from ethyl 3-(3-{5-[4-(2-bromo-5-fluorophenoxy)piperidin-1-yl]-1,3,4-thiadiazol-2-yl}-1,2,4-oxadiazol-5-yl)propanoate and 1N NaOH.

$^1$H NMR (400 MHz, CDCl$_3$): δ7.48-7.52 (m, 1H), 6.61-6.70 (m, 2H), 4.70-4.72 (m, 1H), 3.85-3.92 (m, 2H), 3.77-3.83 (m, 2H), 3.29 (t, 2H), 3.05 (t, 2H), 2.03-2.10 (m, 4H). MS: m/z 498 (MH+).

Example 14

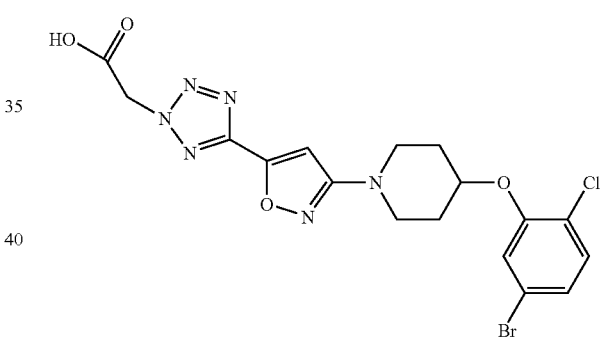

(5-{3-[4-(5-Bromo-2-chlorophenoxy)piperidin-1-yl]isoxazol-5-yl}-2H-tetrazol-2-yl)acetic acid Step 1: 4-(5-Bromo-2-chlorophenoxy)piperidine The title compound was prepared in a similar manner as described for Intermediate 1 from tert-butyl 4-hydroxypiperidine-1-carboxylate and 5-bromo-2-chlorophenol.

Step 2: (5-{3-[4-(5-Bromo-2-chlorophenoxy)piperidin-1-yl]isoxazol-5-yl}-2H-tetrazol-2-yl)acetic acid The title compound was prepared in a similar manner as described for Example 6, steps 3 to 8, from 3-bromo-4,5-dihydroisoxazole-5-carboxamide and 4-(5-bromo-2-chlorophenoxy)piperidine.

$^1$H NMR (500 MHz, acetone-$d_6$): δ7.47 (d, 1H), 7.39 (d, 1H), 7.18 (dd, 1H), 7.01 (s, 1H), 5.81 (s, 2H), 4.94-4.89 (m, 1H), 3.76-3.69 (m, 2H), 3.49-3.42 (m, 2H), 2.20-2.14 (m, 2H), 1.99-1.91 (m, 2H). MS (+ESI): m/z 483, 485 (MH+).

Example 15

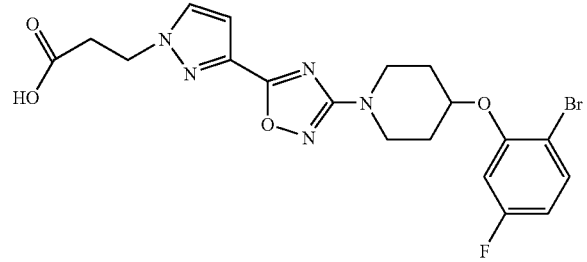

3-(3-{3-[4-(2-bromo-5-fluorophenoxy)piperidin-1-yl]-1,2,4-oxadiazol-5-yl}-1H-pyrazol-1-yl)propanoic acid Step 1: Ethyl 3-(3-{3-[4-(2-bromo-5-fluorophenoxy)piperidin-1-yl]-1,2,4-oxadiazol-5-yl}-1H-pyrazol-1-yl)propanoate The title compound was prepared in a similar manner as described in Example 7 (step 4) from 4-(2-bromo-5-fluorophenoxy)-1-[5-(1H-pyrazol-3-yl)-1,2,4-oxadiazol-3-yl]piperidine, sodium hydride and ethyl 3-bromopropionate and obtained as the more polar major isomer.

$^1$H NMR (500 MHz, acetone-$d_6$): δ7.91-7.86 (m, 1H), 7.62 (dd, 1H), 7.11 (dd, 1H), 6.87 (d, 1H), 6.75 (td, 1H), 4.92-4.88 (m, 1H), 4.58 (t, 2H), 4.15-4.04 (m, 2H), 3.82-3.75 (m, 2H), 3.65-3.53 (m, 2H), 3.00 (t, 2H), 2.17-2.11 (m, 2H), 1.99-1.89 (m, 2H), 1.21 (t, 3H). MS: m/z 508, 510 (MH+).

Step 2: 3-(3-{3-[4-(2-bromo-5-fluorophenoxy)piperidin-1-yl]-1,2,4-oxadiazol-5-yl}-1H-pyrazol-1-yl)propanoic acid To a solution of ethyl 3-(3-{3-[4-(2-bromo-5-fluorophenoxy)piperidin-1-yl]-1,2,4-oxadiazol-5-yl}-1H-pyrazol-1-yl)propanoate (75 mg, 0.148 mmol) in dioxane (492 μL) was added acetic acid (253 μL, 4.43 mmol) and conc. HCl (363 μL, 4.43 mmol). The mixture was heated at 90° C. for 1 h. The solvent was evaporated to one-third its volume, diluted with water (2 mL) and extracted with EtOAc (2×2 mL). The combined organic fractions were extracted with 1N NaOH (1 mL), the aqueous layer was acidified with 2N HCl (1 mL) and extracted with EtOAc (3×2 mL). The combined organic fractions were dried over Na$_2$SO$_4$ and the solvent was evaporated. The product was triturated with hexanes (2×2 mL) and dried under high vacuum to give the title compound.

$^1$H NMR (500 MHz, acetone-$d_6$): δ10.95 (s, 1H), 7.90 (s, 1H), 7.62 (dd, 1H), 7.11 (dd, 1H), 6.87 (s, 1H), 6.75 (td, 1H), 4.90 (d, 1H), 4.57 (t, 2H), 3.83-3.68 (m, 2H), 3.61-3.54 (m, 2H), 3.03 (t, 2H), 2.16-2.11 (m, 2H), 1.96-1.89 (m, 2H). MS: m/z 480, 482 (MH+).

Example 16

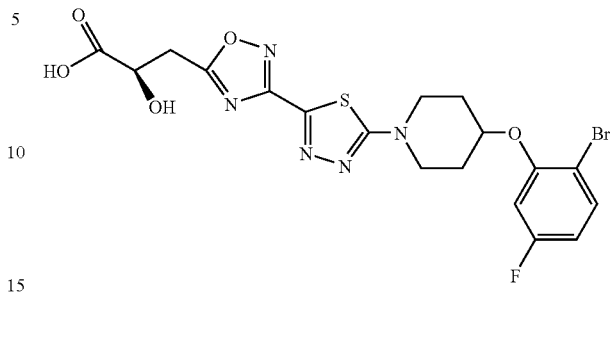

(2R)-3-(3-{5-[4-(2-Bromo-5-fluorophenoxy)piperidin-1-yl]-1,3,4-thiadiazol-2-yl}-1,2,4-oxadiazol-5-yl)-2-hydroxypropanoic acid Step 1: [(4R)-2,2-Dimethyl-5-oxo-1,3-dioxolan-4-yl]acetic acid To a suspension of D-(+)-malic acid (10 g, 75 mmol) in CH$_2$Cl$_2$ (100 mL) was added 2,2-dimethoxypropane (23 g, 225 mmol) and p-toluenesulfonic acid (0.129 g, 0.75 mmol). The reaction mixture was stirred at rt for 4 h, filtered through silica gel (50% EtOAc/hexane) and concentrated to give the title compound.

$^1$H NMR (300 MHz, CDCl$_3$): δ9.70 (s, 1H), 4.69-4.73 (m, 1H), 2.97-3.04 (m, 1H), 2.81-2.89 (m, 1H), 1.62 (s, 3H), 1.57 (s, 3H).

Step 2: [(4R)-2,2-Dimethyl-5-oxo-1,3-dioxolan-4-yl]acetyl fluoride

To a suspension of [(4R)-2,2-dimethyl-5-oxo-1,3-dioxolan-4-yl]acetic acid (100 mg, 0.6 mmol) in CH$_2$Cl$_2$ (2 mL) was added (diethylamino)sulfur trifluoride (DAST) (111 mg, 0.7 mmol) at 0° C. and the resulting solution was stirred at 0° C. for 1 h. More CH$_2$Cl$_2$ (10 mL) was added. The whole mixture was washed with cold water twice, dried over anhydrous Na$_2$SO$_4$, filtered and evaporated in vacuo to afford the title compound. $^1$H NMR (400 MHz, CDCl$_3$): δ4.68-4.71 (m, 1H), 3.11-3.17 (m, 1H), 2.98-3.04 (m, 1H), 1.64 (s, 3H), 1.58 (s, 3H).

Step 3: (5R)-5-[(3-{5-[4-(2-Bromo-5-fluorophenoxy)piperidin-1-yl]-1,3,4-thiadiazol-2-yl}-1,2,4-oxadiazol-5-yl)methyl]-2,2-dimethyl-1,3-dioxolan-4-one The title compound was prepared in a similar manner as described for Example 13, step 2 from 5-[4-(2-bromo-5-fluorophenoxy)piperidin-1-yl]-N'-hydroxy-1,3,4-thiadiazole-2-carboximidamide and [(4R)-2,2-dimethyl-5-oxo-1,3-dioxolan-4-yl]acetyl fluoride.

$^1$H NMR (400 MHz, CDCl$_3$): δ7.51 (dd, 1H), 6.62-6.70 (m, 2H), 5.00 (m, 1H), 4.71 (m, 1H), 3.86-3.93 (m, 2H), 3.78-3.83 (m, 2H), 3.58-3.63 (m, 1H), 3.38-3.44 (m, 1H), 2.04-2.10 (m, 4H), 1.62 (s, 3H), 1.59 (s, 3H).

Step 4: (2R)-3-(3-{5-[4-(2-Bromo-5-fluorophenoxy)piperidin-1-yl]-1,3,4-thiadiazol-2-yl}-1,2,4-oxadiazol-5-yl)-2-hydroxypropanoic acid To a suspension of (5R)-5-[(3-{5-[4-(2-bromo-5-fluorophenoxy)piperidin-1-yl]-1,3,4-thiadiazol-2-yl}-1,2,4-oxadiazol-5-yl)methyl]-2,2-dimethyl-1,3-dioxolan-4-one (200 mg, 0.36 mmol) in MeOH (5 mL) was added KOH (61 mg, 1.08 mmol). The resulted solution was stirred at rt overnight, adjusted to pH 1 with HCl solution (1 mol/L), and then extracted with EtOAc. The combined organic layers were dried over anhydrous $Na_2SO_4$, filtered and evaporated in vacuo. The crude product was purified by preparative HPLC to afford the title compound.

$^1$H NMR (300 MHz, MeOH-$d_4$): δ7.55 (dd, 1H), 7.01 (dd, 1H), 6.65-6.72 (m, 1H), 4.80 (m, 1H), 4.70 (m, 1H), 3.85-3.93 (m, 2H), 3.72-3.80 (m, 2H), 3.48-3.54 (m, 1H), 3.35 (m, 1H), 2.08-2.17 (m, 2H), 1.98-2.06 (m, 2H). MS: m/z 514 (MH$^+$).

Example 17

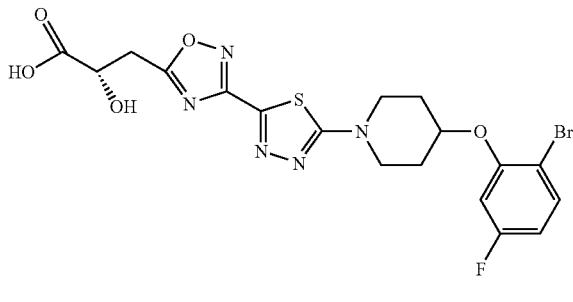

(2S)-3-(3-{5-[4-(2-Bromo-5-fluorophenoxy)piperidin-1-yl]-1,3,4-thiadiazol-2-yl}-1,2,4-oxadiazol-5-yl)-2-hydroxypropanoic acid The title compound was prepared in a similar manner as described for Example 16 from 5-[4-(2-bromo-5-fluorophenoxy)piperidin-1-yl]-N'-hydroxy-1,3,4-thiadiazole-2-carboximidamide and (S)-(−)-malic acid.

$^1$H NMR (400 MHz, acetone-$d_6$): δ7.48 (dd, 1H), 7.00 (dd, 1H), 6.60-6.65 (m, 1H), 4.83-4.87 (m, 1H), 4.50-4.53 (m, 1H), 3.76-3.82 (m, 2H), 3.64-3.70 (m, 2H), 3.37-3.42 (m, 1H), 3.21-3.27 (m, 1H), 2.04-2.11 (m, 2H), 1.90 (m, 2H). MS: m/z 514 (MH$^+$).

Example 18

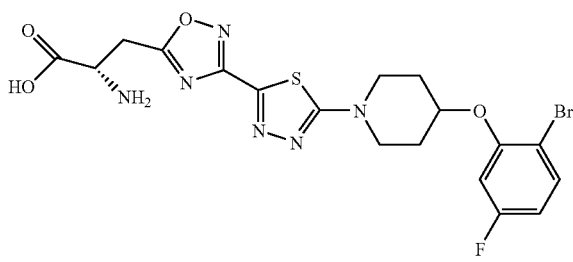

3-(3-{5-[4-(2-Bromo-5-fluorophenoxy)piperidin-1-yl]-1,3,4-thiadiazol-2-yl}-1,2,4-oxadiazol-5-yl)-L-alanine Step 1: N-(Trifluoroacetyl)-L-aspartic acid α-ethyl ester To a suspension of L-aspartic acid (10 g, 75 mmol) in THF was added TFAA (133 g, 635 mmol) during 0.5 h at 0° C. After addition, the suspension was allowed to warm to rt and stirring was continued for 3 h. The solvent was removed in vacuum. The white residue was heated to reflux in EtOH (200 mL) under $N_2$ for 30 min. The solvent was removed in vacuo to afford the title compound. $^1$H NMR (400 MHz, CDCl$_3$): δ7.44 (d, 1H), 4.80-4.84 (m, 1H), 4.27 (q, 2H), 3.15-3.20 (m, 1H), 2.96-3.20 (m, 1H), 1.29 (t, 3H).

Step 2: Ethyl N-(trifluoroacetyl)-L-β-aspartyl chloride

To a solution of N-(trifluoroacetyl)-L-aspartic acid α-ethyl ester (3 g, 11.7 mmol) in dry toluene (15 mL) was added SOCl$_2$ (3 mL). After stirring at reflux for 1 h, the solution was cooled to rt. The mixture was filtered and the solid was washed with cold toluene. The solid was dried to afford the title compound. $^1$H NMR (400 MHz, CDCl$_3$): δ4.71-4.75 (m, 1H), 4.28-2.36 (m, 2H), 3.64-3.70 (m, 1H), 3.56-3.61 (m, 1H), 1.31 (t, J=6 Hz, 3H).

Step 3: Ethyl 3-(3-{5-[4-(2-bromo-5-fluorophenoxy)piperidin-1-yl]-1,3,4-thiadiazol-2-yl}-1,2,4-oxadiazol-5-yl)-N-(trifluoroacetyl)-L-alaninate The title compound was prepared in a similar manner as described for Example 13, step 2 from 5-[4-(2-bromo-5-fluorophenoxy)piperidin-1-yl]-N-hydroxy-1,3,4-thiadiazole-2-carboximidamide and ethyl N-(trifluoroacetyl)-L-β-aspartyl chloride.

$^1$H NMR (400 MHz, CDCl$_3$): δ8.02 (d, 1H), 7.50 (dd, 1H), 6.62-6.70 (m, 2H), 5.05-5.10 (m, 1H), 4.71 (m, 1H), 4.26 (q, 2H), 3.86-3.93 (m, 2H), 3.78-3.83 (m, 2H), 3.66-3.72 (m, 1H), 3.57-3.66 (m, 1H), 2.04-2.10 (m, 4H), 1.26 (t, 3H).

Step 4: 3-(3-{5-[4-(2-Bromo-5-fluorophenoxy)piperidin-1-yl]-1,3,4-thiadiazol-2-yl}-1,2,4-oxadiazol-5-yl)-L-alanine To a suspension of ethyl 3-(3-{5-[4-(2-bromo-5-fluorophenoxy)piperidin-1-yl]-1,3,4-thiadiazol-2-yl}-1,2,4-oxadiazol-5-yl)-N-(trifluoroacetyl)-L-alaninate (550 mg, 0.86 mmol) in EtOH (5 mL) and water (5 mL) was added NaOH (104 mg, 2.6 mmol) and the resulting solution was stirred at rt overnight. The solution was adjusted to pH 7 with HCl solution (1 mol/L), then extracted with EtOAc. The combined organic layers were dried over anhydrous $Na_2SO_4$, filtered and evaporated in vacuo. The crude product was washed with petroleum ether/EtOAc to afford the title compound.

$^1$H NMR (400 MHz, MeOH-$d_4$): δ7.56 (dd, 1H), 7.04 (dd, 1H), 6.68-6.73 (m, 1H), 4.90 (m, 1H), 4.11-4.15 (m, 1H), 3.88-3.95 (m, 2H), 3.76-3.88 (m, 2H), 3.66-3.74 (m, 1H), 3.47-3.52 (m, 1H), 2.10-2.20 (m, 2H), 2.00-2.06 (m, 2H). MS: m/z 513 (MH$^+$).

Example 19

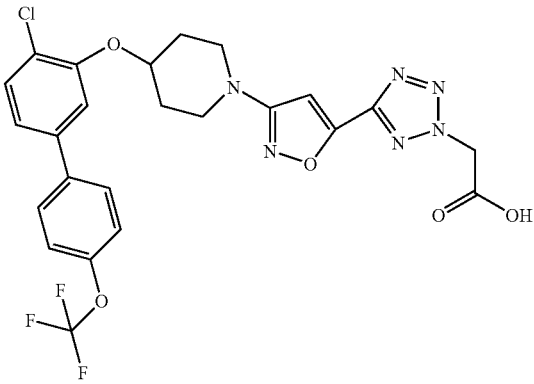

{5-[3-(4-{[4-Chloro-4'-(trifluoromethoxy)biphenyl-3-yl]oxy}piperidin-1-yl)isoxazol-5-yl]-2H-tetrazol-2-yl}acetic acid To a suspension of (5-{3-[4-(5-bromo-2-chlorophenoxy)piperidin-1-yl]isoxazol-5-yl}-2H-tetrazol-2-yl)acetic acid (130 mg, 0.269 mmol), [4-(trifluoromethoxy)phenyl]boronic acid (98 mg, 0.476 mmol) and Pd(Ph$_3$P)$_4$ (25 mg, 0.022 mmol) in toluene (4 mL) was added aqueous 2 M Na$_2$CO$_3$ (1.5 mL, 3.00 mmol). After the resulting heterogeneous mixture was purged with nitrogen, it was gently heated to 80° C. for 6 h with stirring under a nitrogen atmosphere. After cooling to room temperature, the reaction was poured into aqueous 1 N HCl and extracted with EtOAc. The organic layer was washed with brine and dried (Na$_2$SO$_4$). Solvents were removed under reduced pressure and the crude material was purified by column chromatography on silica gel (gradient from 0% to 3% HOAc/EtOAc). After concentration, the white solid was co-evaporated twice and triturated with Et$_2$O/heptane to give the title compound as a white solid. $^1$H NMR (400 MHz, DMSO-d$_6$): δ13.92 (br s, 1H), 7.88-7.83 (m, 2H), 7.57-7.54 (m, 2H), 7.49 (d, 2H), 7.30 (dd, 1H), 7.27 (s, 1H), 5.83 (s, 2H), 5.00-4.93 (m, 1H), 3.68-3.60 (m, 2H), 3.41-3.35 (m, 2H), 2.12-2.02 (s, 2H), 1.87-1.78 (m, 2H). MS: m/z 565 (MH$^+$).

Example 20

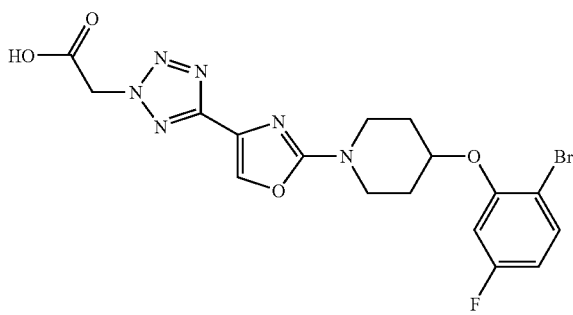

(5-{2-[4-(2-Bromo-5-fluorophenoxy)piperidin-1-yl]-1,3-oxazol-4-yl}-2H-tetrazol-2-yl)acetic acid Step 1: Ethyl-2-[4-(2-bromo-5-fluorophenoxy)piperidin-1-yl]-1,3-oxazole-4-carboxylate To a solution of 4-(2-bromo-5-fluorophenoxy)piperidine (3.281 g, 11.97 mmol) in EtOH (28.5 mL) was added ethyl 2-chlorooxazole-4-carboxylate (1 g, 5.70 mmol) and DIPEA (1.990 mL, 11.39 mmol). The reaction mixture was stirred at rt for 5 h. The solvent was evaporated under reduced pressure. The residue was diluted with 1N HCl and extracted with EtOAc. The combined organic layers were dried (MgSO$_4$), filtered and evaporated under reduced pressure to give the title compound.
$^1$H NMR (500 MHz, acetone-d$_6$): δ8.02 (s, 1H), 7.59 (dd, 1H), 7.08 (dd, 1H), 6.73 (td, 1H), 4.89-4.85 (m, 1H), 4.25 (q, 2H), 3.79-3.72 (m, 2H), 3.64-3.57 (m, 2H), 2.12-2.06 (m, 2H), 1.94-1.86 (m, 2H), 1.28 (t, 3H). MS (+ESI) m/z 413 (MH$^+$)

Step 2: 2-[4-(2-Bromo-5-fluorophenoxy)piperidin-1-yl]-1,3-oxazole-4-carboxamide

Ethyl-2-[4-(2-bromo-5-fluorophenoxy)piperidin-1-yl]-1,3-oxazole-4-carboxylate (2.26 g, 5.47 mmol) was dissolved in MeOH (9 mL) in a sealed tube. The reaction mixture was cooled down to 0° C. and ammonia was bubble into solution for 5 min. The reaction mixture was stirred at 60° C. for 15 h. The solvent was evaporated under reduced pressure. The residue was purified by trituration overnight in ether to afford the title compound.
$^1$H NMR (400 MHz, acetone-d$_6$): δ7.82 (s, 1H), 7.59 (dd, 1H), 7.08 (dd, 1H), 6.96 (s, 1H), 6.73 (d, 1H), 6.52 (s, 1H), 4.90-4.85 (m, 1H), 3.76-3.72 (m, 2H), 3.64-3.60 (m, 2H), 2.10-2.05 (m, 2H), 1.93-1.89 (m, 2H). MS (+ESI) m/z 386 (MH$^+$).

Step 3: 2-[4-(2-Bromo-5-fluorophenoxy)piperidin-1-yl]-1,3-oxazole-4-carbonitrile The title compound was prepared in a similar manner as described for Example 6, step 5 from 2-[4-(2-bromo-5-fluorophenoxy)piperidin-1-yl]-1,3-oxazole-4-carboxamide.
$^1$H NMR (400 MHz, acetone-d$_6$): δ8.24 (s, 1H), 7.59 (dd, 1H), 7.08 (dd, 1H), 6.73 (td, 1H), 4.91-4.87 (m, 1H), 3.77-3.73 (m, 2H), 3.68-3.62 (m, 2H), 2.11-2.05 (m, 2H), 1.95-1.91 (m, 2H). MS (+ESI) m/z 366 (MH$^+$).

Step 4: 4-(2-Bromo-5-fluorophenoxy)-1-[4-(2H-tetrazol-5-yl)-1,3-oxazol-2-yl]piperidine The title compound was prepared in a similar manner as described for Example 11, step 3 from 2-[4-(2-bromo-5-fluorophenoxy)piperidin-1-yl]-1,3-oxazole-4-carbonitrile.
$^1$H NMR (500 MHz, acetone-d$_6$): δ8.21 (s, 1H), 7.61 (dd, 1H), 7.09 (dd, 1H), 6.74 (dt, 1H), 4.92-4.90 (m, 1H), 3.84-3.79 (m, 2H), 3.71-3.67 (m, 2H), 2.16-2.11 (m, 2H), 1.98-1.91 (m, 2H). MS (+ESI) m/z 409 (MH$^+$).

Step 5: Ethyl (5-{2-[4-(2-bromo-5-fluorophenoxy)piperidin-1-yl]-1,3-oxazol-4-yl}-2H-tetrazol-2-yl)acetate The title compound was prepared in a similar manner as described for Example 6, step 7, from 4-(2-bromo-5-fluorophenoxy)-1-[4-(2H-tetrazol-5-yl)-1,3-oxazol-2-yl]piperidine and ethy bromoacetate. The mixture of regioisomers was purified by Combiflash chromatography (SiO$_2$-12 g, gradient elution of 15-50% EtOAc/hexanes over 25 min) to afford the title product as the more polar isomer.

$^1$H NMR (500 MHz, acetone-$d_6$): δ 8.10 (s, 1H), 7.59 (dd, 1H), 7.09 (dd, 1H), 6.74 (dd, 1H), 5.67 (s, 2H), 4.93-4.87 (m, 1H), 4.26 (q, 2H), 3.86-3.79 (m, 2H), 3.71-3.65 (m, 2H), 2.16-2.09 (m, 2H), 1.97-1.91 (m, 2H), 1.27 (t, 3H). MS (+ESI) m/z 495 (MH$^+$).

Step 6: (5-{2-[4-(2-Bromo-5-fluorophenoxy)piperidin-1-yl]-1,3-oxazol-4-yl}-2H-tetrazol-2-yl)acetic acid The title compound was prepared in a similar manner as described for Example 7, step 5 from ethyl (5-{2-[4-(2-bromo-5-fluorophenoxy)piperidin-1-yl]-1,3-oxazol-4-yl}-2H-tetrazol-2-yl)acetate. $^1$H NMR (400 MHz, MeOH-$d_4$): δ 8.10 (s, 1H), 7.59 (t, 1H), 7.10 (d, 1H), 6.73 (t, 1H), 5.69 (s, 2H), 4.85-4.93 (m, 1H), 3.78-3.85 (m, 2H), 3.62-3.72 (m, 2H), 2.08-2.17 (m, 2H), 1.88-1.96 (m, 2H). MS (+ESI) m/z 467 (MH$^+$).

Example 21

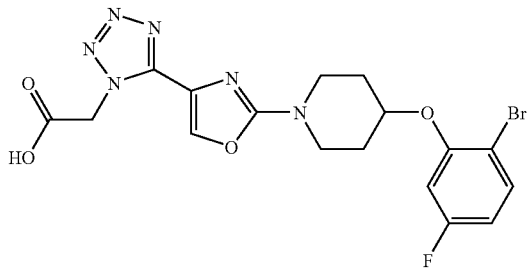

(5-{2-[4-(2-Bromo-5-fluorophenoxy)piperidin-1-yl]-1,3-oxazol-4-yl}-1H-tetrazol-1-yl)acetic acid Step 1: Ethyl (5-{2-[4-(2-bromo-5-fluorophenoxy)piperidin-1-yl]-1,3-oxazol-4-yl}-1H-tetrazol-1-yl)acetate The less polar fractions from Example 20, step 5 were pooled and concentrated to give the title compound. $^1$H NMR (500 MHz, acetone-$d_6$): δ 8.26 (s, 1H), 7.60 (dd, 1H), 7.09 (dd, 1H), 6.74 (td, 1H), 5.68 (s, 2H), 4.93-4.88 (m, 1H), 4.21 (q, 2H), 3.84-3.77 (m, 2H), 3.71-3.64 (m, 2H), 2.16-2.09 (m, 2H), 1.97-1.90 (m, 2H), 1.22 (t, 3H). MS (+ESI) m/z 495 (MH$^+$).

Step 2: (5-{2-[4-(2-Bromo-5-fluorophenoxy)piperidin-1-yl]-1,3-oxazol-4-yl}-1H-tetrazol-1-yl)acetic acid The title compound was prepared in a similar manner as described for Example 7, step 5 from ethyl (5-{2-[4-(2-bromo-5-fluorophenoxy)piperidin-1-yl]-1,3-oxazol-4-yl}-1H-tetrazol-1-yl)acetate.

$^1$H NMR (400 MHz, MeOH-$d_4$): δ 8.25 (s, 1H), 7.59 (t, 1H), 7.10 (d, 1H), 6.73 (t, 1H), 5.69 (s, 2H), 4.85-4.93 (m, 1H), 3.78-3.85 (m, 2H), 3.62-3.72 (m, 2H), 2.08-2.17 (m, 2H), 1.88-1.96 (m, 2H). MS (+ESI) m/z 467 (MH$^+$).

Example of a Pharmaceutical Formulation

As a specific embodiment of an oral pharmaceutical composition of the present invention, a 100 mg potency tablet is composed of 100 mg of any one of Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for a particular condition. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:

1. A compound of structural formula I:

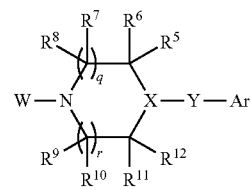

or a pharmaceutically acceptable salt thereof; wherein q is 1;
r is 1;
Z is O, S, or NR$^4$;
X—Y is CR$^{14}$—O;
R$^a$ and R$^b$ are each independently hydrogen or C$_{1-3}$ alkyl, wherein alkyl is optionally substituted with one to three substituents independently selected from fluorine and hydroxy;
W is heteroaryl selected from the group consisting of:

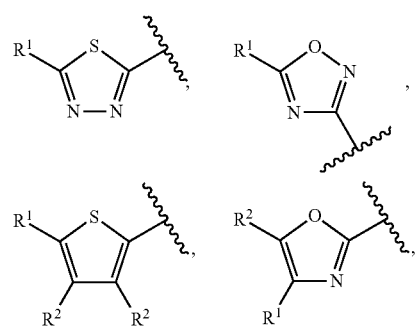

-continued

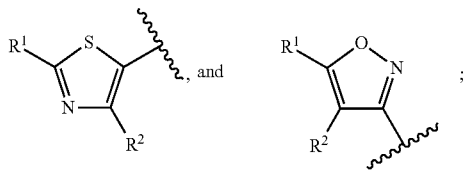

$R^1$ is heteroaryl selected from the group consisting of:

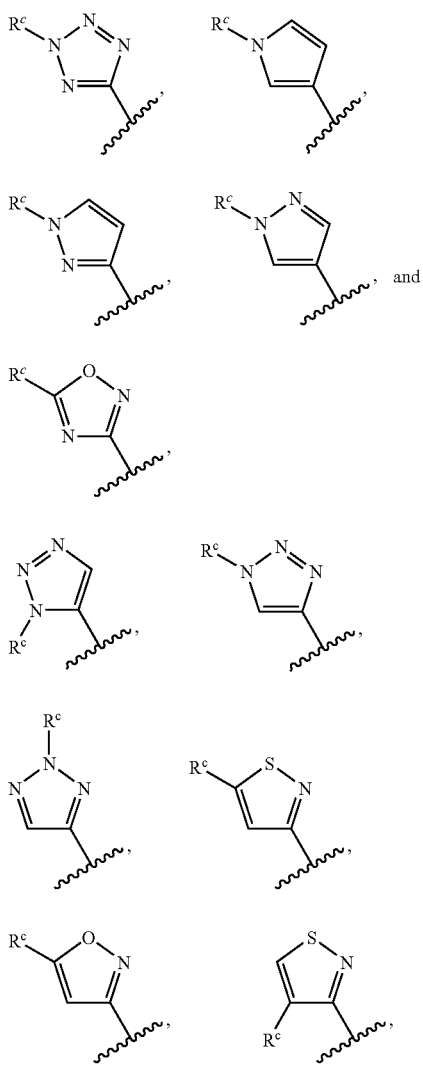

wherein $R^c$ is —$(CH_2)_mCO_2H$, —$(CH_2)_mCO_2C_{1-3}$ alkyl, —$(CH_2)_m$—Z—$(CH_2)_pCO_2H$, or —$(CH_2)_m$—Z—$(CH_2)_pCO_2C_{1-3}$ alkyl; wherein any methylene ($CH_2$) carbon atom in $(CH_2)_m$ or $(CH_2)_p$ is optionally substituted with one hydroxy, one amino, or one to two fluorines; and wherein said $R^1$ heteroaryl ring is optionally substituted with one substituent independently selected from the group consisting of cyano, halogen, $C_{1-4}$ alkyl, $C_{1-4}$ alkoxy, $C_{1-4}$ alkylthio, $C_{1-4}$ alkylsulfonyl, and trifluoromethyl;

each $R^2$ is independently selected from the group consisting of:
hydrogen,
halogen,
hydroxy,
cyano,
amino,
nitro,
$C_{1-4}$ alkyl, optionally substituted with one to five fluorines,
$C_{1-4}$ alkoxy, optionally substituted with one to five fluorines,
$C_{1-4}$ alkylthio, optionally substituted with one to five fluorines,
$C_{1-4}$ alkylsulfonyl,
carboxy,
$C_{1-4}$ alkyloxycarbonyl, and
$C_{1-4}$ alkylcarbonyl;

Ar is phenyl optionally substituted with one to five $R^3$ substituents;

each $R^3$ is independently selected from the group consisting of:
$C_{1-6}$ alkyl,
$C_{2-6}$ alkenyl,
$(CH_2)_n$-phenyl,
$(CH_2)_n$-naphthyl,
$(CH_2)_nC_{3-7}$ cycloalkyl,
halogen,
nitro,
$(CH_2)_nOR^4$,
$(CH_2)_nN(R^4)_2$,
$(CH_2)_nC\equiv N$,
$(CH_2)_nCO_2R^4$,
$(CH_2)_nSO_2N(R^4)_2$,
$(CH_2)_nS(O)_{0-2}R^4$,
$(CH_2)_nNR^4C(O)N(R^4)_2$,
$(CH_2)_nC(O)N(R^4)_2$,
$(CH_2)_nNR^4C(O)R^4$,
$(CH_2)_nNR^4CO_2R^4$,
$(CH_2)_nC(O)R^4$,
$CF_3$,
$CH_2CF_3$,
$OCF_3$, and
$OCH_2CF_3$;

in which phenyl, naphthyl, and cycloalkyl, are optionally substituted with one to three substituents independently selected from halogen, hydroxy, $C_{1-4}$ alkyl, trifluoromethyl, and $C_{1-4}$ alkoxy, optionally substituted with one to five fluorines; and wherein any methylene ($CH_2$) carbon atom in $R^3$ is optionally substituted with one to two groups independently selected from fluorine, hydroxy, and $C_{1-4}$ alkyl; or two substituents when on the same methylene ($CH_2$) group are taken together with the carbon atom to which they are attached to form a cyclopropyl group;

each $R^4$ is independently selected from the group consisting of hydrogen,
$C_{1-6}$ alkyl, and
$(CH_2)_n$-phenyl, wherein alkyl, and phenyl, are optionally substituted with one to three groups independently selected from halogen, $C_{1-4}$ alkyl, and $C_{1-4}$ alkoxy; or two $R^4$ groups together with the atom to which they are attached form a 4- to 8-membered monocyclic ring system optionally containing an additional heteroatom selected from O, S, NH, and $NC_{1-4}$ alkyl;

$R^5, R^6, R^7, R^8, R^9, R^{10}, R^{11}$ and $R^{12}$ are each independently hydrogen;

$R^{13}$ is hydrogen, $C_{1-3}$ alkyl, fluorine, or hydroxy;

each $R^{14}$ is hydrogen;

each m is 1;

each p is independently an integer from 1 to 3;

each n is independently an integer from 0 to 2;

each s is independently an integer from 1 to 3; and each t is independently an integer from 1 to 3.

2. The compound of claim 1 wherein $R^2$ is hydrogen.

3. The compound of claim 1 wherein W is

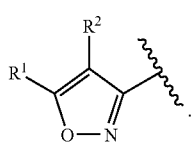

4. The compound of claim 1 wherein $R^1$ is heteroaryl selected from the group consisting of

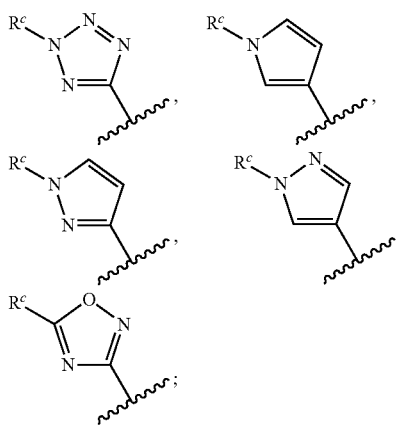

wherein $R^c$ is —$CH_2CO_2H$ or —$CH_2CO_2C_{1-3}$ alkyl.

5. The compound of claim 4 wherein $R^1$ is

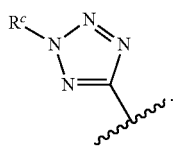

6. The compound of claim 1 wherein q and r are both 1; X—Y is CH—O; W is heteroaryl selected from the group consisting of:

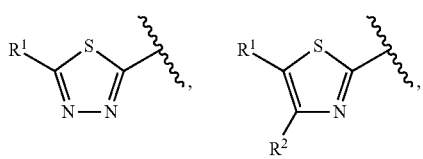

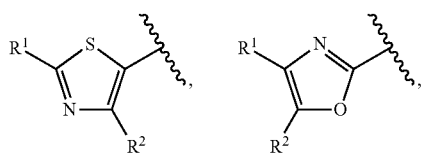

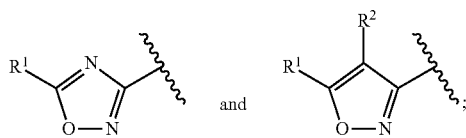

and $R^1$ is heteroaryl selected from the group consisting of:

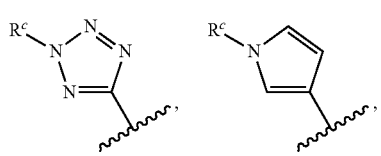

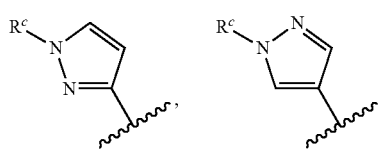

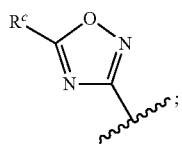

wherein $R^c$ is —$CH_2CO_2H$ or —$CH_2CO_2C_{1-3}$ alkyl.

7. The compound of claim 6 wherein W is

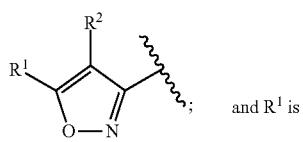 ; and $R^1$ is

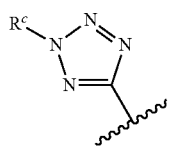

wherein $R^c$ is —$CH_2CO_2H$ or —$CH_2CO_2C_{1-3}$ alkyl.

8. The compound of claim 7 wherein $R^2, R^5, R^6, R^7, R^8, R^9, R^{10}, R^{11}$, and $R^{12}$ are each hydrogen.

9. A compound which is selected from the group consisting of:
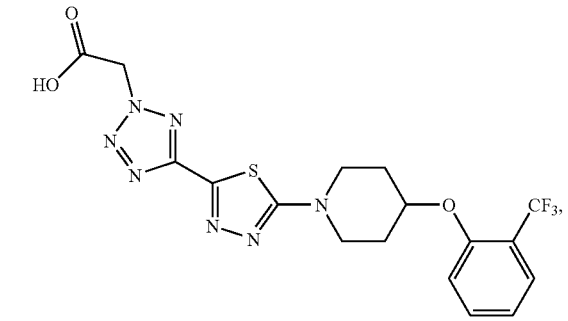
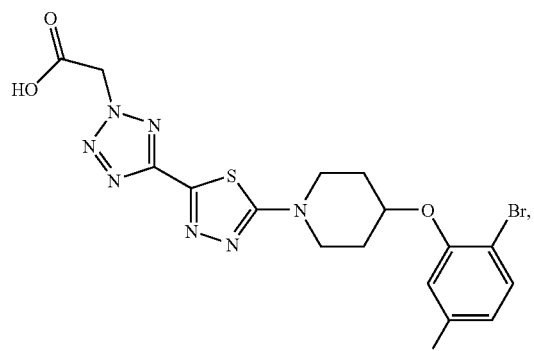
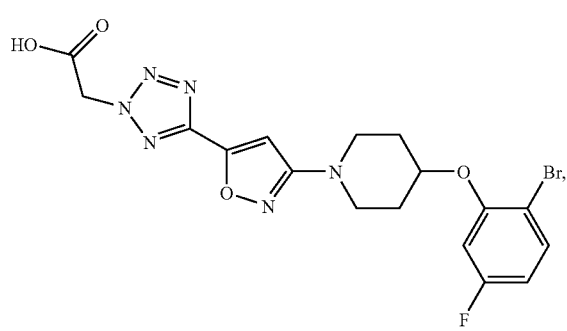
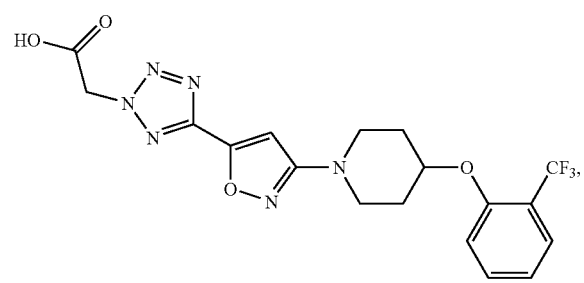
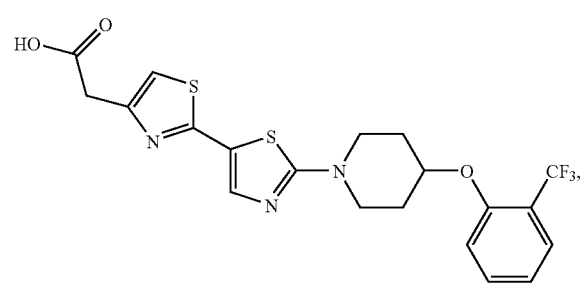
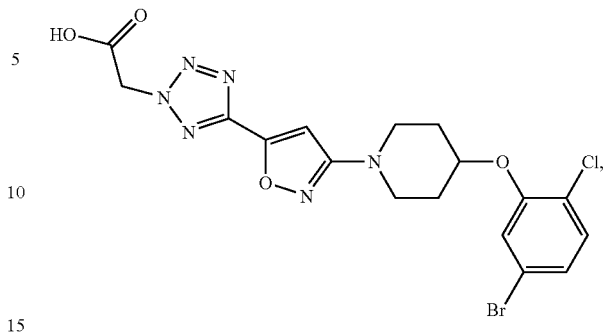
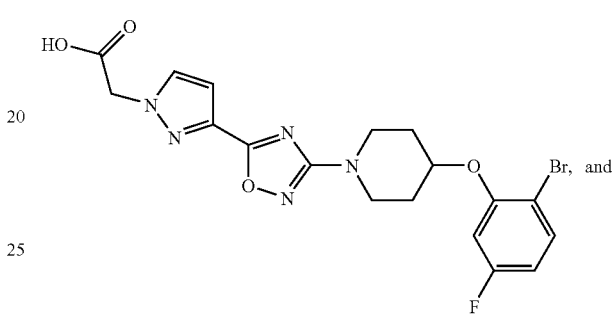
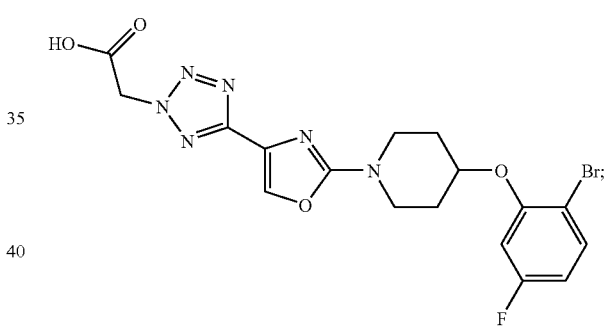
or a pharmaceutically acceptable salt thereof.
10. The compound of claim 9 which is
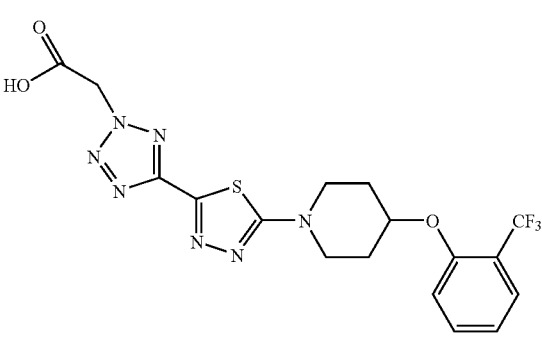
or a pharmaceutically acceptable salt thereof.

11. The compound of claim 9 which is
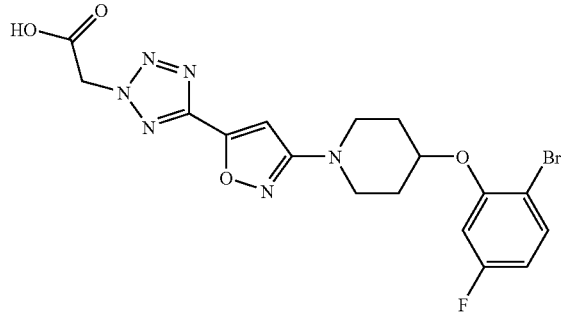
or a pharmaceutically acceptable salt thereof.
12. The compound of claim 9 which is
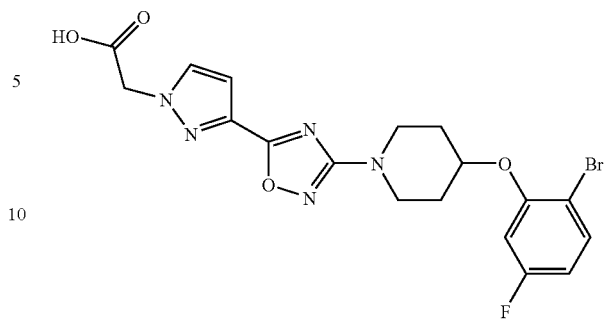
or a pharmaceutically acceptable salt thereof.
13. A pharmaceutical composition comprising a compound in accordance with claim 1 in combination with a pharmaceutically acceptable carrier.
\* \* \* \* \*